(12) United States Patent
Felder et al.

(10) Patent No.: US 10,226,246 B2
(45) Date of Patent: Mar. 12, 2019

(54) TISSUE STAPLER ANVIL FEATURE TO PREVENT PREMATURE JAW OPENING

(71) Applicant: ETHICON ENDO-SURGERY, INC., Cincinnati, OH (US)

(72) Inventors: Kevin D. Felder, Cincinnati, OH (US); John F. Cummings, Madeira, OH (US); Joseph P. Schowalter, South Lebanon, OH (US); Patrick J. Swindon, Cincinnati, OH (US); Johnny H. Alexander, III, West Chester, OH (US); Patrick A. Weizman, Liberty Township, OH (US); Cory G. Kimball, Hamilton, OH (US); Edward G. Chekan, Cincinnati, OH (US); Joseph E. Young, Loveland, OH (US); Christopher C. Miller, Loveland, OH (US); Barry T. Jamison, Fairfield, OH (US); John V. Hunt, Cincinnati, OH (US); Kent P. Baker, Liberty Township, OH (US); Cortney E. Henderson, Loveland, OH (US); Chester O. Baxter, III, Loveland, OH (US); Jerome R. Morgan, Cincinnati, OH (US); Adam R. Dunki-Jacobs, Cincinnati, OH (US); Venkataramanan Mandakolathur Vasudevan, Cincinnati, OH (US); Carl J. Shurtleff, Mason, OH (US); Julia F. Serber, Brookline, MA (US)

(73) Assignee: Ethicon LLC, Guaynabo, PR (US)

( * ) Notice: Subject to any disclaimer, the term of this patent is extended or adjusted under 35 U.S.C. 154(b) by 439 days.

(21) Appl. No.: 14/881,533

(22) Filed: Oct. 13, 2015

(65) Prior Publication Data
US 2016/0030038 A1 Feb. 4, 2016

Related U.S. Application Data

(63) Continuation of application No. 13/344,061, filed on Jan. 5, 2012, now Pat. No. 9,186,148.

(51) Int. Cl.
*A61B 17/072* (2006.01)
*A61B 17/064* (2006.01)
(Continued)

(52) U.S. Cl.
CPC ........ *A61B 17/064* (2013.01); *A61B 17/0686* (2013.01); *A61B 17/072* (2013.01);
(Continued)

(58) Field of Classification Search
CPC ................ A61B 17/068; A61B 17/072; A61B 17/07207; A61B 17/1114; A61B 17/115;
(Continued)

(56) References Cited

U.S. PATENT DOCUMENTS

| 4,319,576 A | 3/1982 | Rothfuss |
| 4,805,823 A | 2/1989 | Rothfuss |

(Continued)

FOREIGN PATENT DOCUMENTS

| EP | 1 616 526 | 1/2006 |
| EP | 2 283 784 | 2/2011 |

(Continued)

OTHER PUBLICATIONS

International Search Report dated Sep. 27, 2013 for Application No. PCT/US2012/069990.
(Continued)

*Primary Examiner* — Scott A. Smith
(74) *Attorney, Agent, or Firm* — Frost Brown Todd LLC

(57) ABSTRACT

A surgical instrument includes a handle assembly having a trigger operable to fire a staple driver to staple tissue. The
(Continued)

instrument includes a pointed rod to which an anvil may be coupled. An anvil detection feature is included to determine when the anvil is coupled to the rod. In some versions, the anvil detection feature comprises a translatable rod that inhibits a lockout feature from disengaging. In other versions, an anvil sensing tube is disposed about the pointed rod and interferes with actuation of the trigger in a first position. A recess in the tube permits trigger to actuate when the anvil sensing tube is in the second position. Alternatively, a resilient tab is coupled to the pointed rod and resists actuation of the staple driver. A trigger lockout assembly may include a spring-loaded button that "pops" out when a push rod is actuated, thereby freeing a pivotable lockout feature.

20 Claims, 28 Drawing Sheets

(51) Int. Cl.
| | | |
|---|---|---|
| A61B 17/068 | (2006.01) | |
| A61B 17/115 | (2006.01) | |
| A61B 17/00 | (2006.01) | |
| A61B 17/29 | (2006.01) | |
| A61B 90/00 | (2016.01) | |

(52) U.S. Cl.
CPC ...... *A61B 17/07207* (2013.01); *A61B 17/115* (2013.01); *A61B 17/1155* (2013.01); *A61B 2017/00876* (2013.01); *A61B 2017/0725* (2013.01); *A61B 2017/07214* (2013.01); *A61B 2017/2946* (2013.01); *A61B 2090/0811* (2016.02)

(58) Field of Classification Search
CPC ...... A61B 17/1155; A61B 2017/07214; A61B 2017/07257; A61B 2017/2946; A61B 17/0686; A61B 17/064; A61B 2017/0725
USPC .. 227/19, 175.2, 175.3, 176.1, 180.1, 179.1, 227/175.1; 606/139, 153, 219
See application file for complete search history.

(56) References Cited

U.S. PATENT DOCUMENTS

| | | | |
|---|---|---|---|
| 5,205,459 A | 4/1993 | Brinkerhoff et al. | |
| 5,271,544 A | 12/1993 | Fox et al. | |
| 5,275,322 A | 1/1994 | Wolf et al. | |
| 5,285,945 A | 2/1994 | Brinkerhoff et al. | |
| 5,292,053 A | 3/1994 | Smith et al. | |
| 5,333,773 A | 8/1994 | Main et al. | |
| 5,350,104 A | 9/1994 | Main et al. | |
| 5,415,334 A | 5/1995 | Williamson et al. | |
| 5,465,895 A | 11/1995 | Knodel et al. | |
| 5,533,661 A | 7/1996 | Main et al. | |
| 5,597,107 A | 1/1997 | Knodel et al. | |
| 5,632,432 A | 5/1997 | Schulze et al. | |
| 5,673,840 A | 10/1997 | Schulze et al. | |
| 5,685,474 A | 11/1997 | Seeber | |
| 5,704,534 A | 1/1998 | Huitema et al. | |
| 5,799,857 A | 9/1998 | Robertson et al. | |
| 5,814,055 A | 9/1998 | Knodel et al. | |
| 5,839,639 A | 11/1998 | Sauer et al. | |
| 6,783,524 B2 | 8/2004 | Anderson et al. | |
| 6,945,444 B2 | 9/2005 | Gresham et al. | |
| 6,978,921 B2 | 12/2005 | Shelton et al. | |
| 7,000,818 B2 | 2/2006 | Shelton et al. | |
| 7,143,923 B2 | 12/2006 | Shelton et al. | |
| 7,303,106 B2 | 12/2007 | Milliman et al. | |
| 7,303,108 B2 | 12/2007 | Shelton | |
| 7,367,485 B2 | 5/2008 | Shelton et al. | |
| 7,380,695 B2 | 6/2008 | Doll et al. | |
| 7,380,696 B2 | 6/2008 | Shelton et al. | |
| 7,404,508 B2 | 7/2008 | Smith et al. | |
| 7,434,715 B2 | 10/2008 | Shelton et al. | |
| 7,721,930 B2 | 5/2010 | McKenna et al. | |
| 7,802,712 B2 | 9/2010 | Milliman et al. | |
| 7,810,692 B2 | 10/2010 | Hall et al. | |
| 7,837,080 B2* | 11/2010 | Schwemberger .... | A61B 17/115 227/175.1 |
| 7,918,377 B2* | 4/2011 | Measamer .......... | A61B 17/1114 227/175.2 |
| 7,975,895 B2 | 7/2011 | Milliman | |
| 7,980,443 B2 | 7/2011 | Scheib et al. | |
| 8,011,554 B2* | 9/2011 | Milliman ............. | A61B 17/115 227/175.1 |
| 8,109,426 B2* | 2/2012 | Milliman ............ | A61B 17/1114 227/175.1 |
| 8,113,405 B2 | 2/2012 | Milliman | |
| 8,136,712 B2 | 3/2012 | Zingman | |
| 8,146,790 B2* | 4/2012 | Milliman ............. | A61B 17/115 227/175.2 |
| 8,181,838 B2 | 5/2012 | Milliman et al. | |
| 8,231,042 B2* | 7/2012 | Hessler ............... | A61B 17/1114 227/175.1 |
| 8,281,974 B2 | 10/2012 | Hessler et al. | |
| 8,322,590 B2* | 12/2012 | Patel ..................... | A61B 17/115 227/176.1 |
| 8,353,438 B2* | 1/2013 | Baxter, III ......... | A61B 1/00087 227/175.1 |
| 8,393,514 B2 | 3/2013 | Shelton, IV et al. | |
| 8,496,157 B2* | 7/2013 | Olson ................ | A61B 17/1155 227/176.1 |
| 8,636,766 B2* | 1/2014 | Milliman .......... | A61B 17/07207 227/175.2 |
| 8,708,212 B2* | 4/2014 | Williams ........... | A61B 17/1155 227/175.1 |
| 8,794,497 B2* | 8/2014 | Zingman ............... | A61B 17/072 227/175.2 |
| 8,800,841 B2* | 8/2014 | Ellerhorst ........ | A61B 17/07207 227/175.1 |
| 8,899,466 B2* | 12/2014 | Baxter, III ........... | A61B 17/115 227/179.1 |
| 9,010,605 B2* | 4/2015 | Olson ................ | A61B 17/1155 227/175.1 |
| 9,186,148 B2 | 11/2015 | Felder et al. | |

FOREIGN PATENT DOCUMENTS

| | | |
|---|---|---|
| JP | 2003-523255 A | 8/2003 |
| JP | 4388745 B2 | 12/2009 |
| JP | 2010-214127 A | 9/2010 |
| WO | WO 97/34533 | 9/1997 |
| WO | WO 01/62164 | 8/2001 |
| WO | WO 03/034926 | 5/2003 |

OTHER PUBLICATIONS

International Preliminary Report on Patentability and Written Opinion dated Jul. 8, 2014 for Application No. PCT/US2012/069990.
Japanese Office Action dated Dec. 6, 2016 for Application No. JP 2014-551259, 4 pgs.
Chinese Office Action, The First Office Action, dated Feb. 4, 2016 for Application No. CN 201280066141.2, 20 pgs.
Chinese Search Report dated Jan. 26, 2016 for Application No. CN 201280066141.2, 2 pgs.
Chinese Search Report, Supplemental, dated Jul. 10, 2016 for Application No. CN 201280066141.2, 1 pg.
Chinese Office Action, Notification to Grant Patent Rights for Invention, dated Aug. 9, 2016 for Application No. CN 201280066141. 2, 3 pgs.
European Examination Report dated Apr. 11, 2017 for Application No. EP 12814065.4, 6 pgs.
Japanese Search Report dated Nov. 29, 2016 for Application No. JP 2014-551259, 34 pgs.
Japanese Office Action, Decision of Refusal, dated May 9, 2017 for Application No. JP 2014-551259, 7 pgs.
Japanese Office Action, Decision to Grant a Patent, dated Sep. 5, 2017 for Application No. JP 2014-551259, 6 pgs.

(56) References Cited

OTHER PUBLICATIONS

Russian Office Action dated Sep. 27, 2016 for Application No. RU 2014132163/14, 3 pgs.

* cited by examiner

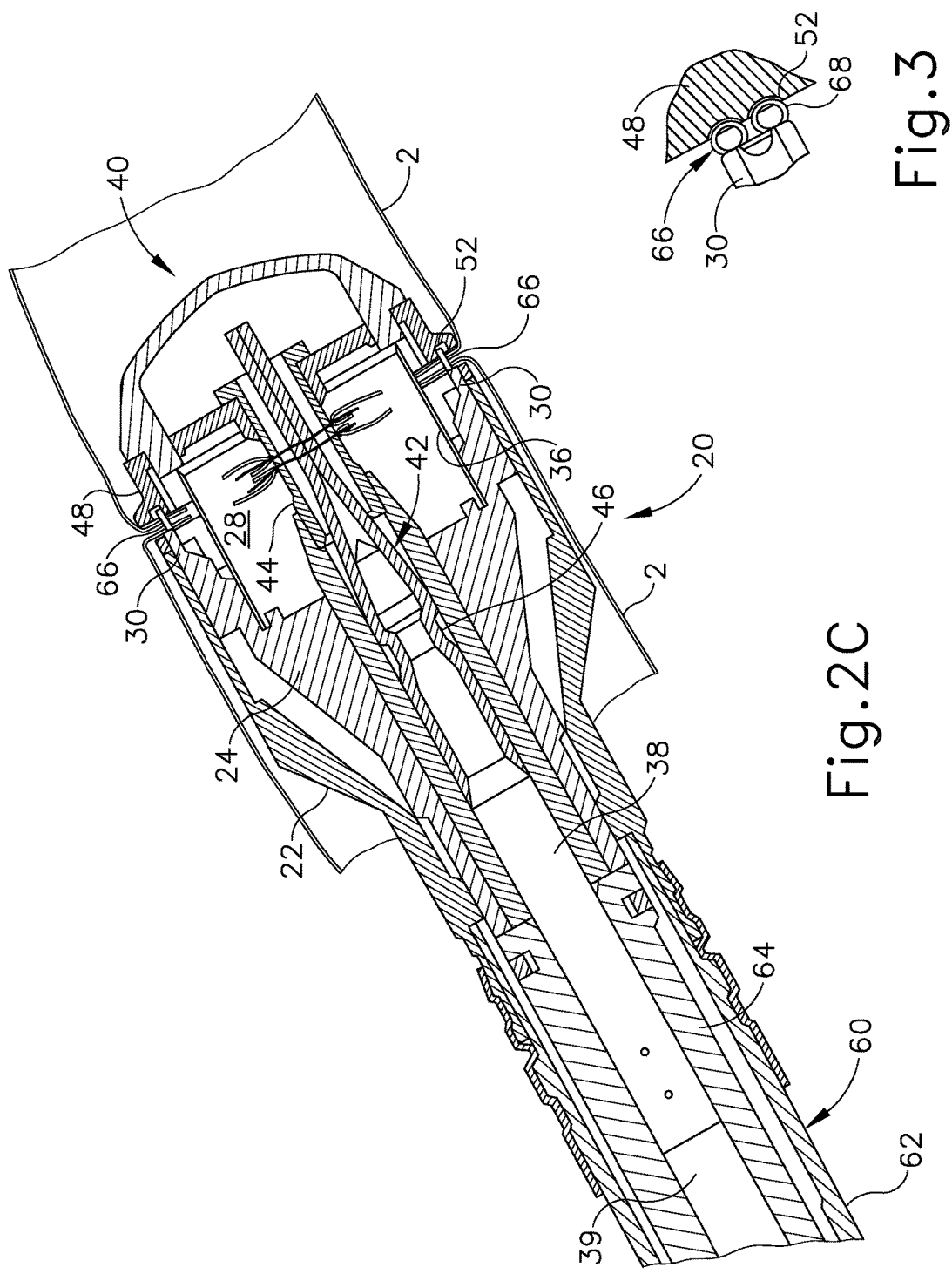

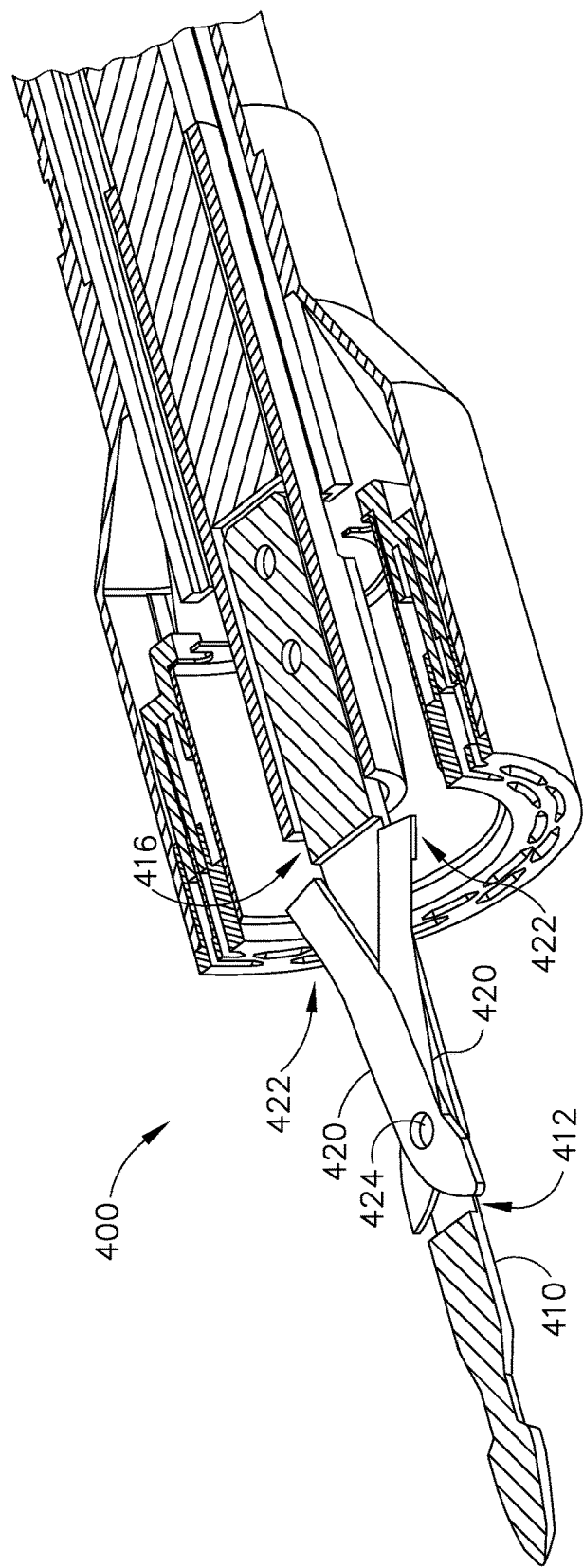

TISSUE STAPLER ANVIL FEATURE TO PREVENT PREMATURE JAW OPENING

This application is a continuation of U.S. patent application Ser. No. 13/344,061, entitled "Tissue Stapler Anvil Feature to Prevent Premature Jaw Opening", filed on Jan. 5, 2012, and issued as U.S. Pat. No. 9,186,148 on Nov. 17, 2015.

BACKGROUND

In some settings, a surgeon may want to position a surgical instrument through an orifice of the patient and use the instrument to adjust, position, attach, and/or otherwise interact with tissue within the patient. For instance, in some surgical procedures, portions of the gastrointestinal tract may be cut and removed to eliminate undesirable tissue or for other reasons. Once the desired tissue is removed, the remaining portions will need to be recoupled together. One such tool for accomplishing these anastomotic procedures is a circular stapler that is inserted through a patient's orifice.

Examples of such circular surgical staplers are described in U.S. Pat. No. 5,205,459, entitled "Surgical Anastomosis Stapling Instrument," issued Apr. 27, 1993; U.S. Pat. No. 5,271,544, entitled "Surgical Anastomosis Stapling Instrument," issued Dec. 21, 1993; U.S. Pat. No. 5,275,322, entitled "Surgical Anastomosis Stapling Instrument," issued Jan. 4, 1994; U.S. Pat. No. 5,285,945, entitled "Surgical Anastomosis Stapling Instrument," issued Feb. 15, 1994; U.S. Pat. No. 5,292,053, entitled "Surgical Anastomosis Stapling Instrument," issued Mar. 8, 1994; U.S. Pat. No. 5,333,773, entitled "Surgical Anastomosis Stapling Instrument," issued Aug. 2, 1994; U.S. Pat. No. 5,350,104, entitled "Surgical Anastomosis Stapling Instrument," issued Sep. 27, 1994; and U.S. Pat. No. 5,533,661, entitled "Surgical Anastomosis Stapling Instrument," issued Jul. 9, 1996. The disclosure of each of the above-cited U.S. Patents is incorporated by reference herein. Some such staplers are operable to clamp down on layers of tissue, cut through the clamped layers of tissue, and drive staples through the layers of tissue to substantially seal the severed layers of tissue together near the severed ends of the tissue layers.

Merely additional other exemplary surgical staplers are disclosed in U.S. Pat. No. 4,805,823, entitled "Pocket Configuration for Internal Organ Staplers," issued Feb. 21, 1989; U.S. Pat. No. 5,415,334, entitled "Surgical Stapler and Staple Cartridge," issued May 16, 1995; U.S. Pat. No. 5,465,895, entitled "Surgical Stapler Instrument," issued Nov. 14, 1995; U.S. Pat. No. 5,597,107, entitled "Surgical Stapler Instrument," issued Jan. 28, 1997; U.S. Pat. No. 5,632,432, entitled "Surgical Instrument," issued May 27, 1997; U.S. Pat. No. 5,673,840, entitled "Surgical Instrument," issued Oct. 7, 1997; U.S. Pat. No. 5,704,534, entitled "Articulation Assembly for Surgical Instruments," issued Jan. 6, 1998; U.S. Pat. No. 5,814,055, entitled "Surgical Clamping Mechanism," issued Sep. 29, 1998; U.S. Pat. No. 6,978,921, entitled "Surgical Stapling Instrument Incorporating an E-Beam Firing Mechanism," issued Dec. 27, 2005; U.S. Pat. No. 7,000,818, entitled "Surgical Stapling Instrument Having Separate Distinct Closing and Firing Systems," issued Feb. 21, 2006; U.S. Pat. No. 7,143,923, entitled "Surgical Stapling Instrument Having a Firing Lockout for an Unclosed Anvil," issued Dec. 5, 2006; U.S. Pat. No. 7,303,108, entitled "Surgical Stapling Instrument Incorporating a Multi-Stroke Firing Mechanism with a Flexible Rack," issued Dec. 4, 2007; U.S. Pat. No. 7,367,485, entitled "Surgical Stapling Instrument Incorporating a Multistroke Firing Mechanism Having a Rotary Transmission," issued May 6, 2008; U.S. Pat. No. 7,380,695, entitled "Surgical Stapling Instrument Having a Single Lockout Mechanism for Prevention of Firing," issued Jun. 3, 2008; U.S. Pat. No. 7,380,696, entitled "Articulating Surgical Stapling Instrument Incorporating a Two-Piece E-Beam Firing Mechanism," issued Jun. 3, 2008; U.S. Pat. No. 7,404,508, entitled "Surgical Stapling and Cutting Device," issued Jul. 29, 2008; U.S. Pat. No. 7,434,715, entitled "Surgical Stapling Instrument Having Multistroke Firing with Opening Lockout," issued Oct. 14, 2008; and U.S. Pat. No. 7,721,930, entitled "Disposable Cartridge with Adhesive for Use with a Stapling Device," issued May 25, 2010. The disclosure of each of the above-cited U.S. Patents is incorporated by reference herein. While the surgical staplers referred to above are described as being used in endoscopic procedures, it should be understood that such surgical staplers may also be used in open procedures and/or other non-endoscopic procedures.

While various kinds of surgical stapling instruments and associated components have been made and used, it is believed that no one prior to the inventor(s) has made or used the invention described in the appended claims.

BRIEF DESCRIPTION OF THE DRAWINGS

While the specification concludes with claims which particularly point out and distinctly claim this technology, it is believed this technology will be better understood from the following description of certain examples taken in conjunction with the accompanying drawings, in which like reference numerals identify the same elements and in which:

FIG. 2C depicts an enlarged longitudinal cross-sectional view of the stapling head assembly of FIG. 2A showing an exemplary staple driver and blade in a fired position;

FIG. 3 depicts an enlarged partial cross-sectional view of an exemplary staple formed against the anvil;

FIG. 9A depicts a partial cross-sectional view on an alternative anvil detection assembly having a pair of spring clips, shown in an extended position;

Figure 6:
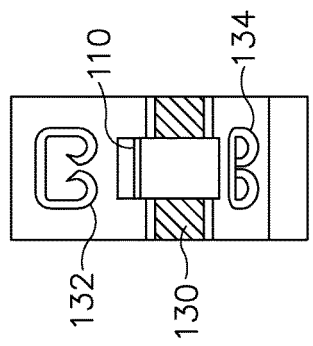
FIG. 6 depicts an diagrammatic view of the indicator window of FIG. 5 showing an exemplary indicator bar and exemplary corresponding staple representations.

The drawings are not intended to be limiting in any way, and it is contemplated that various embodiments of the technology may be carried out in a variety of other ways, including those not necessarily depicted in the drawings. The accompanying drawings incorporated in and forming a part of the specification illustrate several aspects of the present technology, and together with the description serve to explain the principles of the technology; it being understood, however, that this technology is not limited to the precise arrangements shown.

DETAILED DESCRIPTION

The following description of certain examples of the technology should not be used to limit its scope. Other examples, features, aspects, embodiments, and advantages of the technology will become apparent to those skilled in the art from the following description, which is by way of illustration, one of the best modes contemplated for carrying out the technology. As will be realized, the technology described herein is capable of other different and obvious aspects, all without departing from the technology. Accordingly, the drawings and descriptions should be regarded as illustrative in nature and not restrictive.

I. Overview of Exemplary Circular Stapling Surgical Instrument

FIGS. 1-6 depict an exemplary circular surgical stapling instrument (10) having a stapling head assembly (20), a shaft assembly (60), and an actuator handle assembly (70), each of which will be described in more detail below. Shaft assembly (60) extends distally from actuator handle assembly (70) and stapling head assembly (20) is coupled to a distal end of shaft assembly (60). In brief, actuator handle assembly (70) is operable to actuate a staple driver (24) of stapling head assembly (20) to drive a plurality of staples (66) out of stapling head assembly (20). Staples (66) are bent to form completed staples by an anvil (40) that is attached at the distal end of instrument (10). Accordingly, tissue (2), shown in FIGS. 2A-2C, may be stapled utilizing instrument (10).

In the present example, instrument (10) comprises a closure system and a firing system. The closure system comprises a trocar (38), a trocar actuator (39), and a rotating knob (98). An anvil (40) may be coupled to a distal end of trocar (38). Rotating knob (98) is operable to longitudinally translate trocar (38) relative to stapling head assembly (20), thereby translating anvil (40) when anvil (40) is coupled to trocar (38), to clamp tissue between anvil (40) and stapling head assembly (20). The firing system comprises a trigger (74), a trigger actuation assembly (84), a driver actuator (64), and a staple driver (24). Staple driver (24) includes a knife (36) configured to sever tissue when staple driver (24) is actuated longitudinally. In addition, staples (66) are positioned distal to a plurality of staple driving members (30) of staple driver (24) such that staple driver (24) also drives staples (66) distally when staple driver (24) is actuated longitudinally. Thus, when trigger (74) is actuated and trigger actuation assembly (84) actuates staple driver (24) via driver actuator (64), knife (36) and members (30) substantially simultaneously sever tissue (2) and drive staples (66) distally relative to stapling head assembly (20) into tissue. The components and functionalities of the closure system and firing system will now be described in greater detail.

A. Exemplary Anvil

Figure 1:
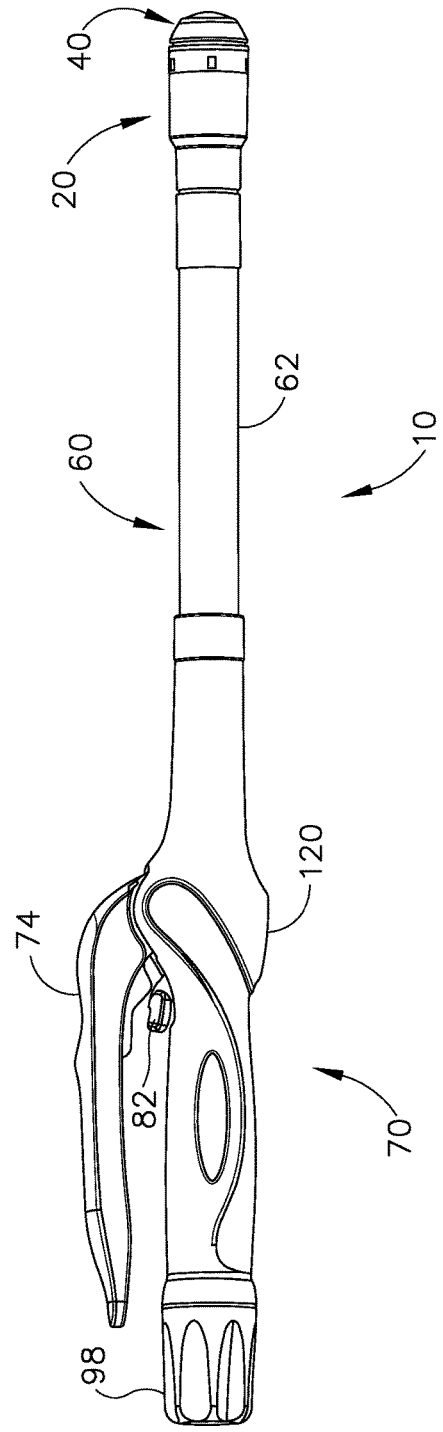
FIG. 1 depicts a side elevation view of an exemplary circular stapling surgical instrument.
Figure 2A:
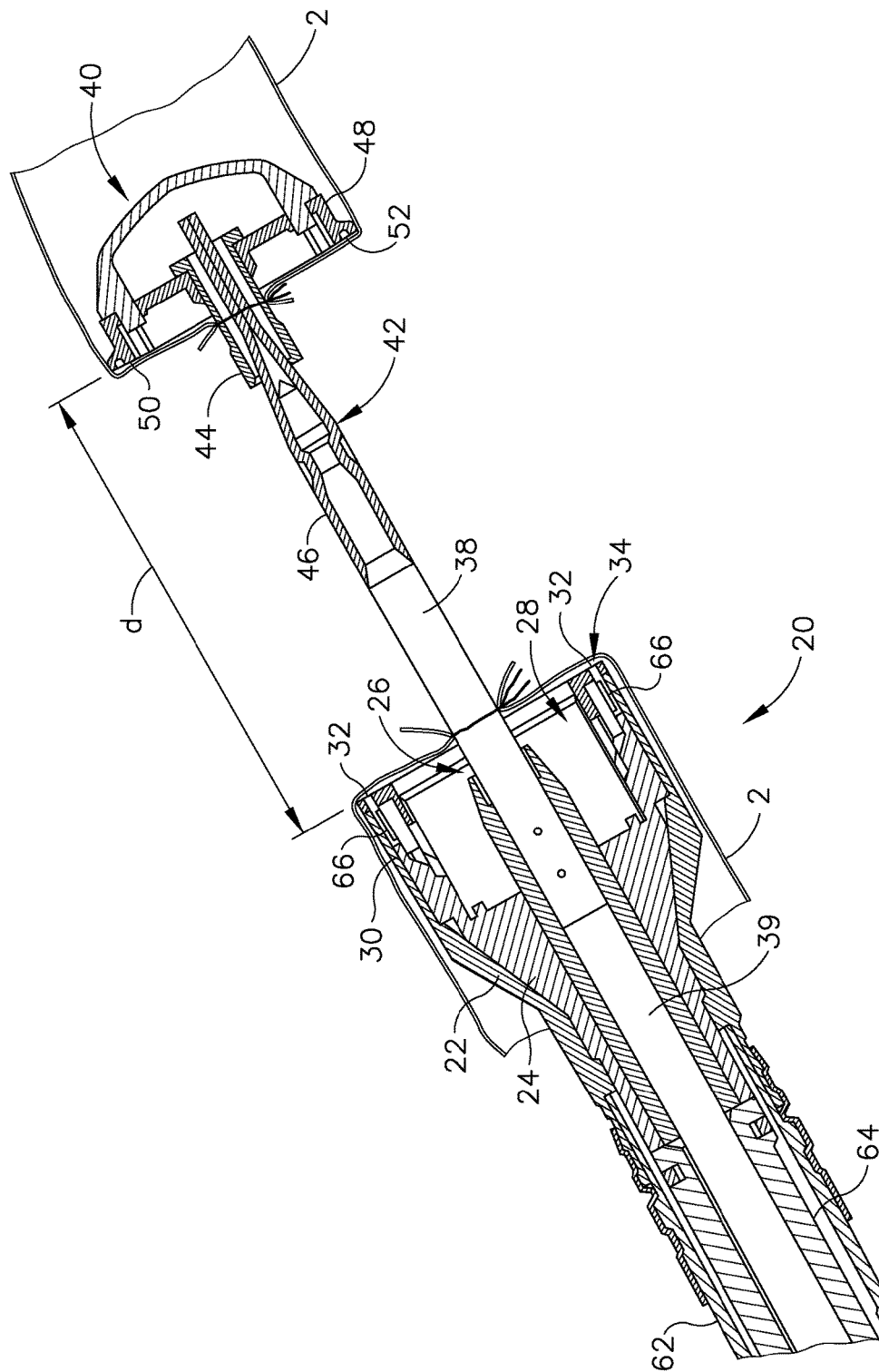
FIG. 2A depicts an enlarged longitudinal cross-section view of an exemplary stapling head assembly of the instrument of FIG. 1 showing an exemplary anvil in an open position.
Figure 2B:
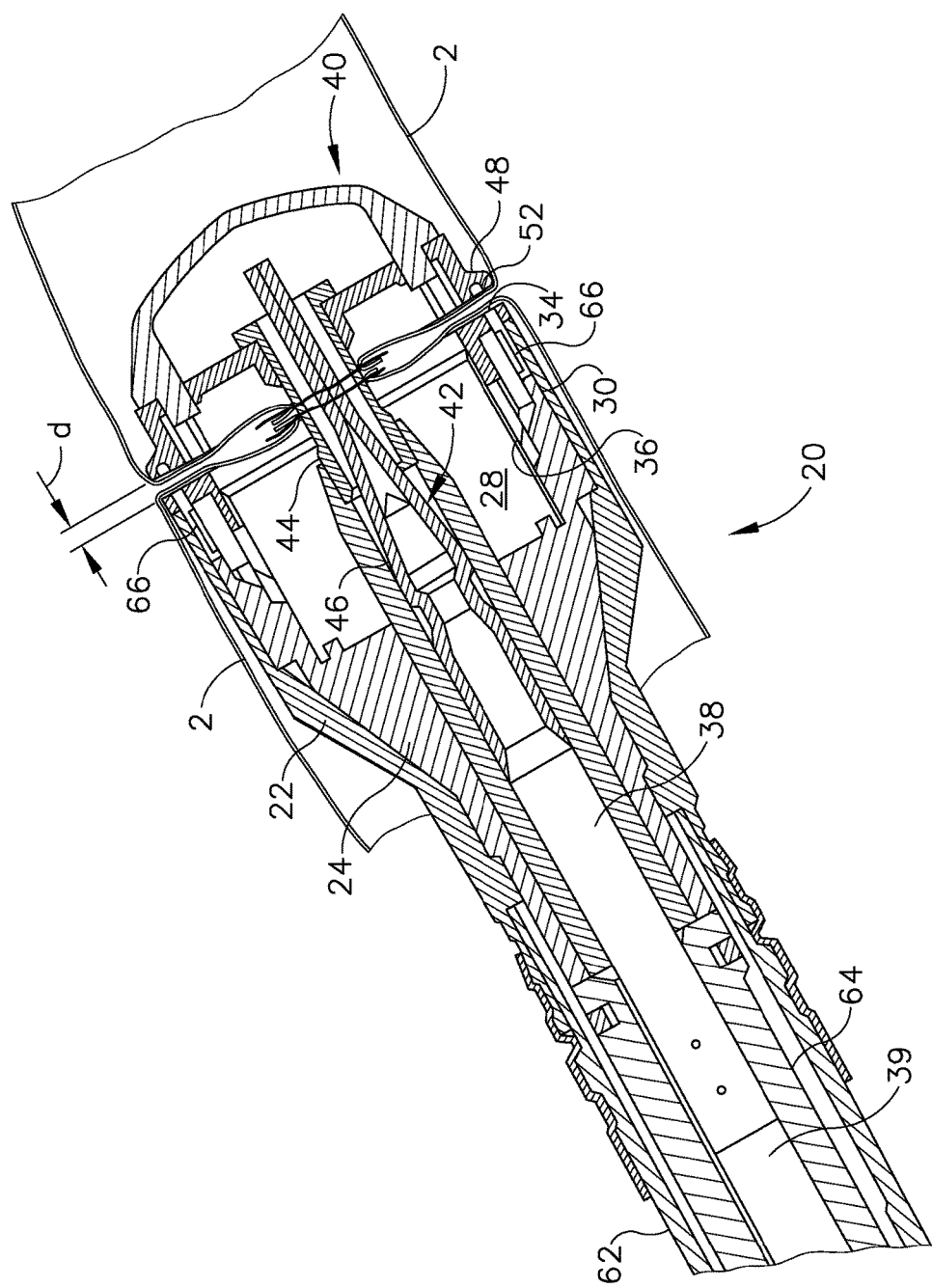
FIG. 2B depicts an enlarged longitudinal cross-sectional view of the stapling head assembly of FIG. 2A showing the anvil in a closed position.

As shown in FIGS. 1-2C, anvil (40) is selectively coupleable to instrument (10) to provide a surface against which staples (66) may be bent to staple material contained between stapling head assembly (20) and anvil (40). Anvil (40) of the present example is selectively coupleable to a trocar or pointed rod (38) that extends distally relative to stapling head assembly (20). Referring to FIGS. 2A-2C, anvil (40) is selectively coupleable via the coupling of a proximal shaft (42) of anvil (40) to a distal tip of trocar (38). Anvil (40) comprises a generally circular anvil head (48) and a proximal shaft (42) extending proximally from anvil head (48). In the example shown, proximal shaft (42) comprises a tubular member (44) having resiliently biased retaining clips (46) to selectively couple anvil (40) to trocar (38), though this is merely optional, and it should be understood that other retention features for coupling anvil (40) to trocar (38) may be used as well. For example, C-clips, clamps, threading, pins, adhesives, etc. may be employed to couple anvil (40) to trocar (38). In addition, while anvil (40) is described as selectively coupleable to trocar (38), in some versions proximal shaft (42) may include a one-way coupling feature such that anvil (40) cannot be removed from trocar (38) once anvil (40) is attached. Merely exemplary one-way features include barbs, one way snaps, collets, collars, tabs, bands, etc. Of course still other configurations for coupling anvil (40) to trocar (38) will be apparent to one of ordinary skill in the art in view of the teachings herein. For instance, trocar (38) may instead be a hollow shaft and proximal shaft (42) may comprise a sharpened rod that is insertable into the hollow shaft.

Anvil head (48) of the present example comprises a plurality of staple forming pockets (52) formed in a proximal face (50) of anvil head (48). Accordingly, when anvil (40) is in the closed position and staples (66) are driven out of stapling head assembly (20) into staple forming pockets (52), as shown in FIG. 2C, legs (68) of staples (66) are bent to form completed staples. It should be understood that staple forming pockets (52) are merely optional and may be omitted in some versions.

With anvil (40) as a separate component, it should be understood that anvil (40) may be inserted and secured to a portion of tissue (2) prior to being coupled to stapling head assembly (20). By way of example only, anvil (40) may be inserted into and secured to a first tubular portion of tissue (2) while instrument (10) is inserted into and secured to a second tubular portion of tissue (2). For instance, the first tubular portion of tissue (2) may be sutured to or about a portion of anvil (40), and the second tubular portion of tissue (2) may be sutured to or about trocar (38).

As shown in FIG. 2A, anvil (40) is then coupled to trocar (38). Trocar (38) of the present example is shown in a distal most actuated position. Such an extended position for trocar (38) may provide a larger area to which tissue (2) may be coupled prior to attachment of anvil (40). In addition, the extended position of trocar (38) may also provide for easier attachment of anvil (40) to trocar (38). Trocar (38) further includes a tapered distal tip. Such a tip may be capable of piercing through tissue and/or aiding the insertion of anvil (40) on to trocar (38), though the tapered distal tip is merely optional. For instance, in other versions trocar (38) may have a blunt tip. In addition, or in the alternative, trocar (38) may include a magnetic portion (not shown) which may attract anvil (40) towards trocar (38). Of course still further configurations and arrangements for anvil (40) and trocar (38) will be apparent to one of ordinary skill in the art in view of the teachings herein.

When anvil (40) is coupled to trocar (38), the distance between a proximal face of the anvil (40) and a distal face of stapling head assembly (20) defines a gap distance d. Trocar (38) of the present example is translatable longitudinally relative to stapling head assembly (20) via an adjusting knob (98) located at a proximal end of actuator handle assembly (70), as will be described in greater detail below. Accordingly, when anvil (40) is coupled to trocar (38), rotation of adjusting knob (98) enlarges or reduces gap distance d by actuating anvil (40) relative to stapling head assembly (20). For instance, as shown sequentially in FIGS. 2A-2B, anvil (40) is shown actuating proximally relative to actuator handle assembly (70) from an initial, open position to a closed position, thereby reducing the gap distance d and the distance between the two portions of tissue (2) to be joined. Once the gap distance d is brought within a predetermined range, stapling head assembly (20) may be fired, as shown in FIG. 2C, to staple and sever tissue (2) between anvil (40) and stapling head assembly (20). Stapling head assembly (20) is operable to staple and sever tissue (2) by a user pivoting a trigger (74) of actuator handle assembly (70), as will be described in greater detail below.

Figure 5:
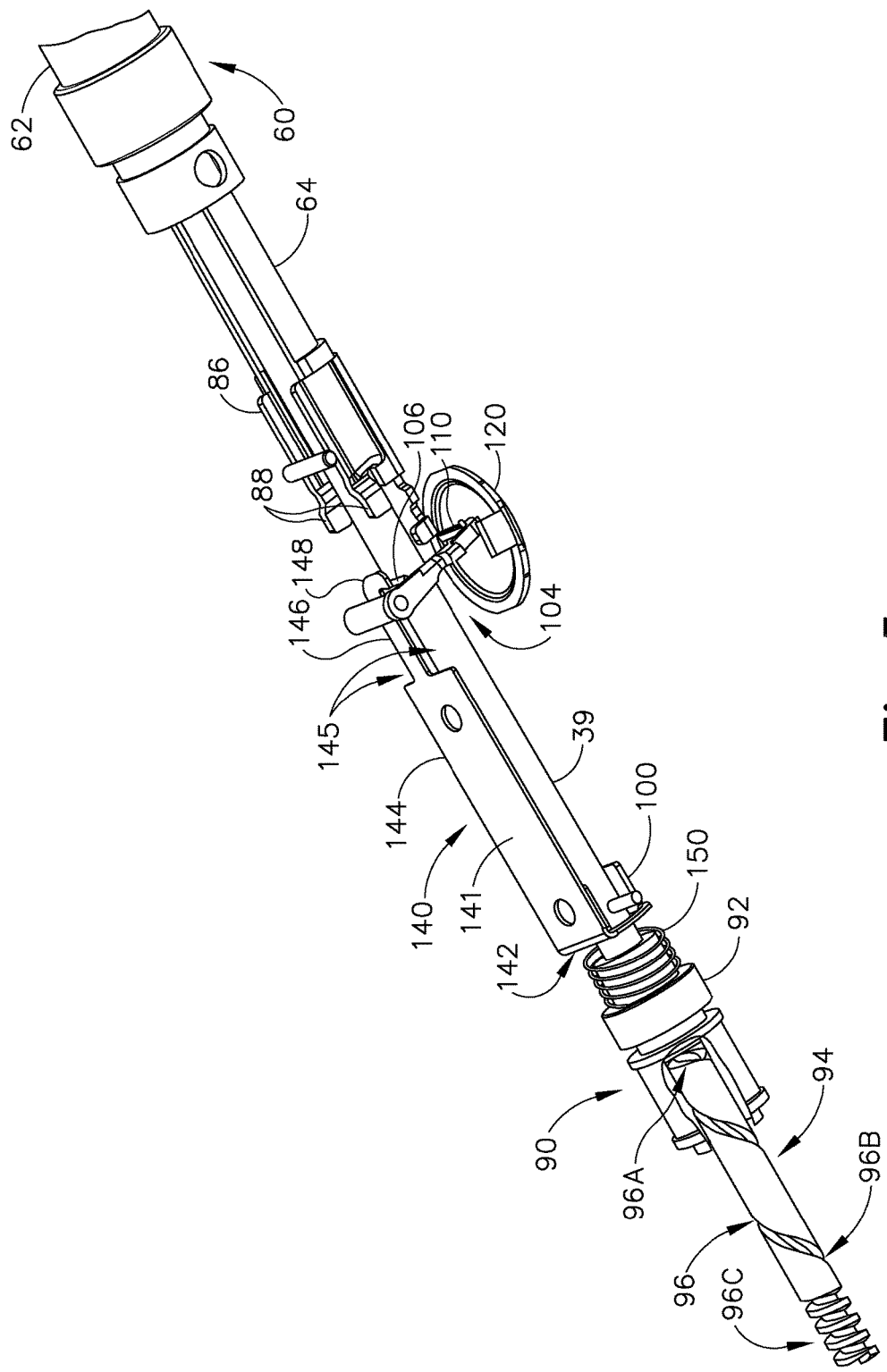
FIG. 5 depicts an enlarged partial perspective view of an exemplary indicator assembly of the surgical instrument of FIG. 1 showing an indicator window and indicator lever.

As noted above, gap distance d corresponds to the distance between anvil (40) and stapling head assembly (20). When instrument (10) is inserted into a patient, this gap distance d may not be easily viewable. Accordingly, a moveable indicator bar (110), shown in FIGS. 5-6, is provided to be visible through an indicator window (120) positioned opposite to trigger (74). Indicator bar (110) is operable to move in response to rotation of adjusting knob (98) such that the position of indicator bar (110) is representative of the gap distance d. As shown in FIG. 6, indicator window (120) further comprises a scale (130) which indicates that the anvil gap is within a desired operating range (e.g., a green colored region or "green zone") and a corresponding staple compression representation at each end of scale (130). By way of example only, as shown in FIG. 6, a first staple image (132) depicts a large staple height while a second staple image (134) depicts a small staple height. Accordingly, a user can view the position of the coupled anvil (40) relative to the stapling head assembly (20) via indicator bar (110) and scale (130). The user may then adjust the positioning of anvil (40) via adjusting knob (98) accordingly.

Referring back to FIGS. 2A-2C, a user sutures a portion of tissue (2) about tubular member (44) such that anvil head (48) is located within a portion of the tissue (2) to be stapled. When tissue (2) is attached to anvil (40), retaining clips (46)

and a portion of tubular member (44) protrude out from tissue (2) such that the user may couple anvil (40) to trocar (38). With tissue (2) coupled to trocar (38) and/or another portion of stapling head assembly (20), the user attaches anvil (40) to trocar (38) and actuates anvil (40) proximally towards stapling head assembly (20) to reduce the gap distance d. Once instrument (10) is within the operating range, the user then staples together the ends of tissue (2), thereby forming a substantially contiguous tubular portion of tissue (2).

Anvil (40) may be further constructed in accordance with at least some of the teachings of U.S. Pat. No. 5,205,459; U.S. Pat. No. 5,271,544; U.S. Pat. No. 5,275,322; U.S. Pat. No. 5,285,945; U.S. Pat. No. 5,292,053; U.S. Pat. No. 5,333,773; U.S. Pat. No. 5,350,104; U.S. Pat. No. 5,533,661, the disclosures of which are incorporated by reference herein; and/or in accordance with other configurations as will be apparent to one of ordinary skill in the art in view of the teachings herein.

B. Exemplary Stapling Head Assembly

Stapling head assembly (20) of the present example is coupled to a distal end of shaft assembly (60) and comprises a tubular casing (22) housing a slidable staple driver (24) and a plurality of staples (66) contained within staple pockets (32). Staples (66) and staple pockets (32) are disposed in a circular array about tubular casing (22). In the present example, staples (66) and staple pockets (32) are disposed in a pair of concentric annular rows of staples (66) and staple pockets (32). Staple driver (24) is operable to actuate longitudinally within tubular casing (22) in response to rotation of trigger (74) of actuator handle assembly (70). As shown in FIGS. 2A-2C, staple driver (24) comprises a flared cylindrical member having a trocar opening (26), a central recess (28), and a plurality of members (30) disposed circumferentially about central recess (28) and extending distally relative to shaft assembly (60). Each member (30) is configured to contact and engage a corresponding staple (66) of the plurality of staples (66) within staple pockets (32). Accordingly, when staple driver (24) is actuated distally relative to actuator handle assembly (70), each member (30) drives a corresponding staple (66) out of its staple pocket (32) through a staple aperture (34) formed in a distal end of tubular casing (22). Because each member (30) extends from staple driver (24), the plurality of staples (66) are driven out of stapling head assembly (20) at substantially the same time. When anvil (40) is in the closed position, staples (66) are driven into staple forming pockets (52) to bend legs (68) of the staples (66), thereby stapling the material located between anvil (40) and stapling head assembly (20). FIG. 3 depicts one merely exemplary staple (66) driven by a member (30) into a staple forming pocket (32) of anvil (40) to bend legs (68).

Staple driver (24) further includes a cylindrical knife (36) that is coaxial to trocar opening (26) and inset from staple pockets (32). In the present example, cylindrical knife (36) is disposed within central recess (28) to translate distally with staple driver (24). When anvil (40) is secured to trocar (38), as described above, anvil head (48) provides a surface against which cylindrical knife (36) cuts the material contained between anvil (40) and stapling head assembly (20). In some versions, anvil head (48) may include a recess (not shown) for cylindrical knife (36) to aid in cutting the material (e.g., by providing a cooperative shearing edge). In addition, or in the alternative, anvil head (48) may include one or more opposing cylindrical knives (not shown) offset from cylindrical knife (36) such that a scissor-type cutting action may be provided. Still other configurations will be apparent to one of ordinary skill in the art in view of the teachings herein. Stapling head assembly (20) is thus operable to both staple and cut tissue (2) substantially simultaneously in response to actuation by actuator handle assembly (70).

Of course stapling head assembly (20) may be further constructed in accordance with at least some of the teachings of U.S. Pat. No. 5,205,459; U.S. Pat. No. 5,271,544; U.S. Pat. No. 5,275,322; U.S. Pat. No. 5,285,945; U.S. Pat. No. 5,292,053; U.S. Pat. No. 5,333,773; U.S. Pat. No. 5,350,104; U.S. Pat. No. 5,533,661, the disclosures of which are incorporated by reference herein; and/or in accordance with other configurations as will be apparent to one of ordinary skill in the art in view of the teachings herein.

As noted previously, staple driver (24) includes a trocar opening (26). Trocar opening (26) is configured to permit trocar (38) to longitudinally slide relative to stapling head assembly (20) and/or shaft assembly (60). As shown in FIGS. 2A-2C, trocar (38) is coupled to a trocar actuator (39) such that trocar (38) can be actuated longitudinally via rotation of rotating knob (98), as will be described in greater detail below in reference to actuator handle assembly (70). In the present example, trocar actuator (39) comprises an elongated, relatively stiff shaft coupled to trocar (38), though this is merely optional. In some versions, actuator (39) may comprise a longitudinally stiff material while permitting lateral bending such that portions of instrument (10) may be selectively bent or curved during use; or instrument (10) may include a preset bent shaft assembly (60). One merely exemplary material is nitinol. When anvil (40) is coupled to trocar (38), trocar (38) and anvil (40) are translatable via actuator (39) to adjust the gap distance d between anvil (40) and stapling head assembly (20). Still further configurations for actuator (39) to longitudinally actuate trocar (38) will be apparent to one of ordinary skill in the art in view of the teachings herein.

C. Exemplary Shaft Assembly

Stapling head assembly (20) and trocar (38) are positioned at a distal end of shaft assembly (60), as shown in FIGS. 2A-2C. Shaft assembly (60) of the present example comprises an outer tubular member (62) and a driver actuator (64). Outer tubular member (62) is coupled to tubular casing (22) of stapling head assembly (20) and to a body (72) of actuator handle assembly (70), thereby providing a mechanical ground for the actuating components therein. The proximal end of driver actuator (64) is coupled to a trigger actuation assembly (84) of actuator handle assembly (70), described below. The distal end of driver actuator (64) is coupled to staple driver (24) such that the rotation of trigger (74) longitudinally actuates staple driver (24). As shown in FIGS. 2A-2C, driver actuator (64) comprises a tubular member having an open longitudinal axis such that actuator (39) coupled to trocar (38) may actuate longitudinally within and relative to driver actuator (64). Of course it should be understood that other components may be disposed within driver actuator (64) as will be apparent to one of ordinary skill in the art in view of the teachings herein.

Shaft assembly (60) may be further constructed in accordance with at least some of the teachings of U.S. Pat. No. 5,205,459; U.S. Pat. No. 5,271,544; U.S. Pat. No. 5,275,322; U.S. Pat. No. 5,285,945; U.S. Pat. No. 5,292,053; U.S. Pat. No. 5,333,773; U.S. Pat. No. 5,350,104; U.S. Pat. No. 5,533,661, the disclosures of which are incorporated by reference herein; and/or in accordance with other configurations as will be apparent to one of ordinary skill in the art in view of the teachings herein.

D. Exemplary Actuator Handle Assembly

Figure 4A:
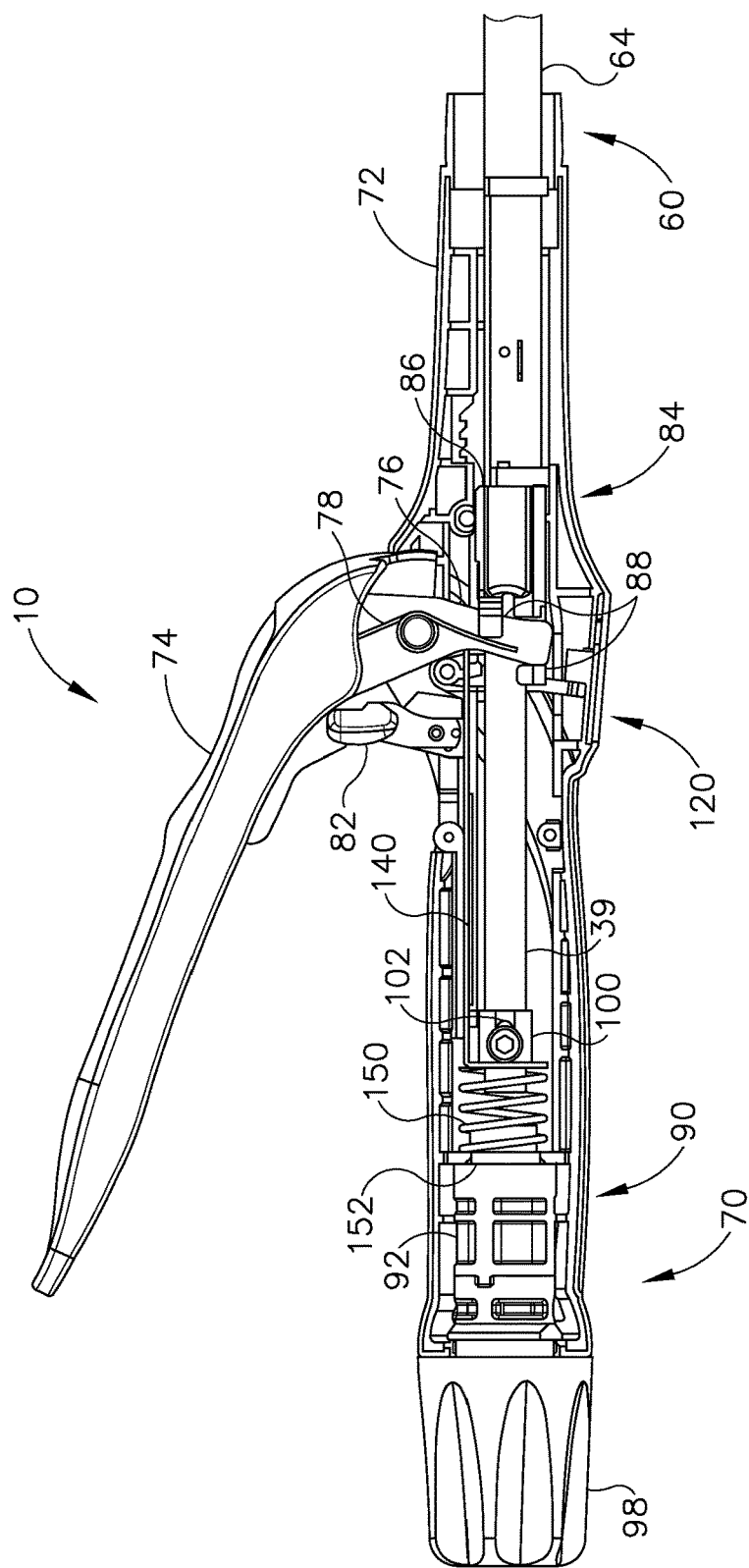
FIG. 4A depicts an enlarged side elevation view of an exemplary actuator handle assembly of the surgical instrument of FIG. 1 with a portion of the body removed, showing a trigger in an unfired position and a lockout feature in a locked position.
Figure 4B:
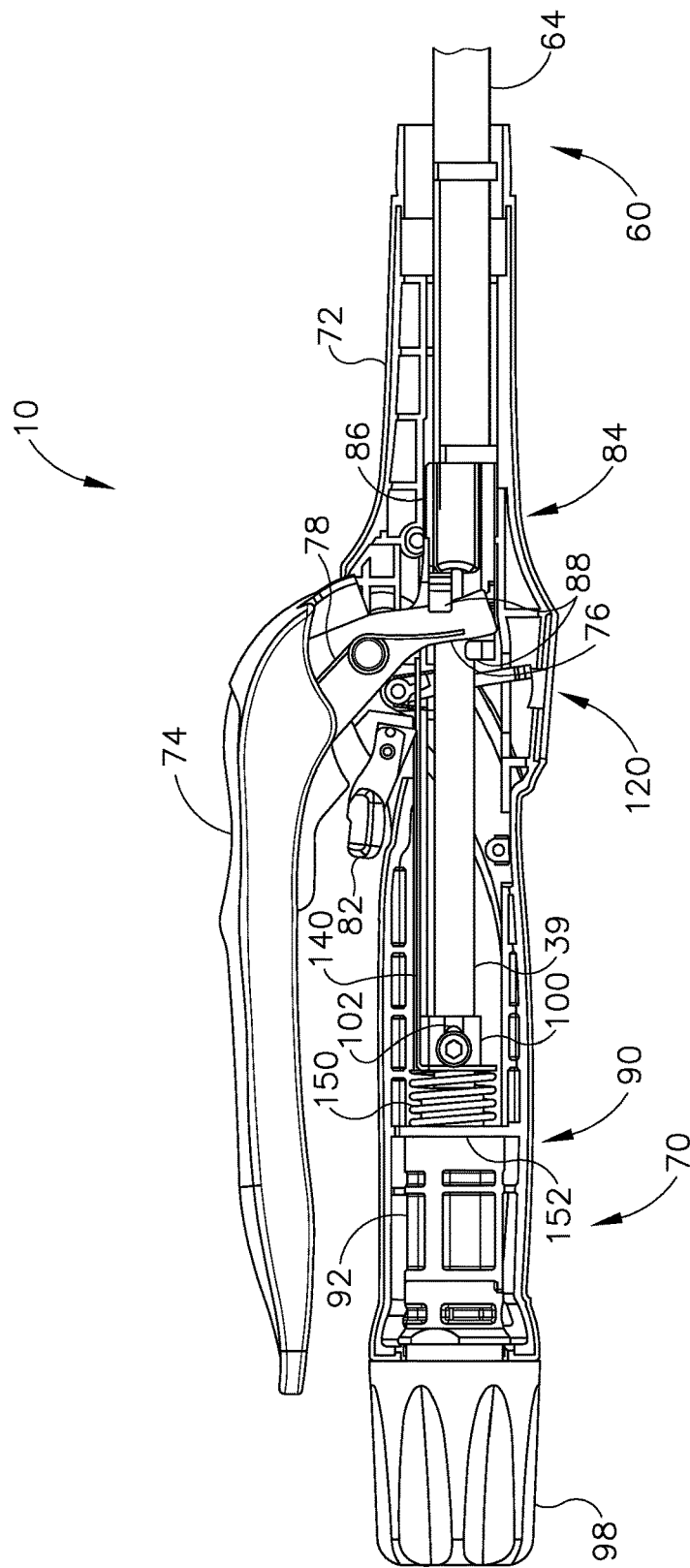
FIG. 4B depicts an enlarged side elevation view of the actuator handle assembly of FIG. 4A, showing the trigger in a fired position and the lockout feature in an unlocked position.

Referring now to FIGS. 4A-5, actuator handle assembly (70) comprises a body (72), a trigger (74), a lockout feature (82), a trigger actuation assembly (84), and a trocar actuation assembly (90). Trigger (74) of the present example is pivotably mounted to body (72) and is coupled to trigger actuation assembly (84) such that rotation of trigger (74) from an unfired position (shown in FIG. 4A) to a fired position (shown in FIG. 4B) actuates driver actuator (64) described above. A spring (78) is coupled to body (72) and trigger (74) to bias trigger (74) towards the unfired position. Lockout feature (82) is a pivotable member that is coupled to body (72). In a first, locked position, lockout feature (82) is pivoted upwards and away from body (72) such that lockout feature (82) engages trigger (74) and mechanically resists actuation of trigger (74) by a user. In a second, unlocked position, such as that shown in FIGS. 1 and 4B, lockout feature (82) is pivoted downward such that trigger (74) may be actuated by the user. Accordingly, with lockout feature (82) in the second position, trigger (74) can engage a trigger actuation assembly (84) to fire instrument (10).

As shown in FIGS. 4A-4B, trigger actuation assembly (84) of the present example comprises a slidable trigger carriage (86) engaged with a proximal end of driver actuator (64). Carriage (86) includes a set of tabs (88) on a proximal end of carriage (86) to retain and engage a pair of trigger arms (76) extending from trigger (74). Accordingly, when trigger (74) is pivoted, carriage (86) is actuated longitudinally and transfers the longitudinal motion to driver actuator (64). In the example shown, carriage (86) is fixedly coupled to the proximal end of driver actuator (64), though this is merely optional. Indeed, in one merely exemplary alternative, carriage (86) may simply abut driver actuator (64) while a distal spring (not shown) biases driver actuator (64) proximally relative to actuator handle assembly (70).

Trigger actuation assembly (84) may be further constructed in accordance with at least some of the teachings of U.S. Pat. No. 5,205,459; U.S. Pat. No. 5,271,544; U.S. Pat. No. 5,275,322; U.S. Pat. No. 5,285,945; U.S. Pat. No. 5,292,053; U.S. Pat. No. 5,333,773; U.S. Pat. No. 5,350,104; U.S. Pat. No. 5,533,661, the disclosures of which are incorporated by reference herein; and/or in accordance with other configurations as will be apparent to one of ordinary skill in the art in view of the teachings herein.

Body (72) also houses a trocar actuation assembly (90) configured to actuate trocar (38) longitudinally in response to rotation of adjusting knob (98). As best shown in FIGS. 4A-5, trocar actuation assembly (90) of the present example comprises adjusting knob (98), a grooved shank (94), and a sleeve (92). Grooved shank (94) of the present example is located at a distal end of trocar actuator (39), though it should be understood that grooved shank (94) and trocar actuator (39) may alternatively be separate components that engage to transmit longitudinal movement. Adjusting knob (98) is rotatably supported by the proximal end of body (72) and is operable to rotate sleeve (92) that is engaged with grooved shank (94) via an internal tab (not shown). Grooved shank (94) of the present example comprises a continuous groove (96) formed in the outer surface of grooved shank (94). Accordingly, when adjusting knob (98) is rotated, the internal tab rides within groove (96) and grooved shank (94) is longitudinally actuated relative to sleeve (92). Since grooved shank (94) is located at the distal end of trocar actuator (39), rotating adjusting knob (98) in a first direction advances trocar actuator (39) distally relative to actuator handle assembly (70). Accordingly, the gap distance d between anvil (40) and stapling head assembly (20) is increased. By rotating adjusting knob (98) in the opposite direction, trocar actuator (39) is actuated proximally relative to actuator handle assembly (70) to reduce the gap distance d between anvil (40) and stapling head assembly (20). Thus, trocar actuation assembly (90) is operable to actuate trocar (38) in response to rotating adjustment knob (98). Of course other configurations for trocar actuation assembly (90) will be apparent to one of ordinary skill in the art in view of the teachings herein.

Groove (96) of the present example comprises a plurality of different portions (96A, 96B, 96C) that have a varying pitch or number of grooves per axial distance. The present groove (96) is divided into a distal portion (96A), a middle portion (96B) and a proximal portion (96C). As shown in FIG. 5, distal portion (96A) comprises a fine pitch or a high number of grooves over a short axial distance of grooved shank (94) such that a large number of rotations of adjusting knob (98) are required to traverse the short axial distance. Middle portion (96B) comprises a section with comparably coarser pitch or fewer grooves per axial distance such that relatively few rotations are required to traverse a long axial distance. Accordingly, the gap distance d may be quickly reduced through relatively few rotations of adjusting knob (98). Proximal portion (96C) of the present example is substantially similar to distal portion (96A) and comprises a fine pitch or a high number of grooves over a short axial distance of grooved shank (94) such that a large number of rotations are required to traverse the short axial distance. Proximal portion (96C) of the present example is positioned within sleeve (92) when anvil (40) is substantially near to stapling head assembly (20) such that indicator bar (110) moves within indicator window (120) along scale (130) to indicate that the anvil gap is within a desired operating range, as will be described in more detail below. Accordingly, when the tab is within proximal portion (96C) of groove (96), each rotation of adjusting knob (98) may reduce the gap distance d by a small amount to provide for fine tuning.

Trocar actuation assembly (90) may be further constructed in accordance with at least some of the teachings of U.S. Pat. No. 5,205,459; U.S. Pat. No. 5,271,544; U.S. Pat. No. 5,275,322; U.S. Pat. No. 5,285,945; U.S. Pat. No. 5,292,053; U.S. Pat. No. 5,333,773; U.S. Pat. No. 5,350,104; U.S. Pat. No. 5,533,661, the disclosures of which are incorporated by reference herein; and/or in accordance with other configurations as will be apparent to one of ordinary skill in the art in view of the teachings herein.

In the example shown in FIGS. 4A-4B, a U-shaped clip (100) is attached to an intermediate portion of trocar actuator (39) located distally of grooved shank (94). U-shaped clip (100) engages with a portion of body (72) to substantially prevent trocar actuator (39) from rotating about its axis when adjusting knob (98) is rotated. U-shaped clip (100) further includes an elongated slot (102) on each of its opposite sides for receiving an attachment member, such as a screw, bolt, pin, clip, etc., to selectively adjust the longitudinal position of elongated slot (102) of U-shaped clip (100) relative to trocar actuator (39) for purposes of calibrating indicator bar (110) relative to scale (130).

As shown in FIG. 5, actuator handle assembly (70) further includes an indicator bracket (140) configured to engage and pivot an indicator (104). Indicator bracket (140) of the present example is slidable relative to body (72) along a pair of slots formed on body (72). Indicator bracket (140) comprises a rectangular plate (144), an indicator arm (146), and an angled flange (142). Angled flange (142) is formed at the proximal end of rectangular plate (144) and includes an aperture (not shown) to slidable mount onto trocar actuator (39) and/or grooved shank (94). A coil spring (150) is interposed between flange (142) and a boss (152) to bias flange (142) against U-shaped clip (100). Accordingly, when U-shaped clip (100) actuates distally with trocar actuator (39) and/or grooved shank (94), coil spring (150) urges indicator bracket (140) to travel distally with U-shaped clip (100). In addition, U-shaped clip (100) urges indicator bracket (140) proximally relative to boss (152) when trocar actuator (39) and/or grooved shank (94) translate proximally, thereby compressing coil spring (150). Of course, it should be understood that in some versions indicator bracket (140) may be fixedly attached to trocar actuator (39) and/or grooved shank (94).

In the present example, a portion of lockout feature (82) abuts a surface (141) of indicator bracket (140) when indicator bracket (140) is in a longitudinal position that does not correspond to when the anvil gap is within a desired operating range (e.g., a green colored region or "green zone"). When the anvil gap is within a desired operating range (e.g., a green colored region or "green zone"), indicator bracket (140) narrows to provide a pair of gaps (145) on either side of an indicator arm (146) that permits lockout feature (82) to pivot, thereby releasing trigger (74). Accordingly, lockout feature (82) and indicator bracket (140) can substantially prevent a user from releasing and operating trigger (74) until anvil (40) is in a predetermined operating range. Of course it should be understood that lockout feature (82) may be omitted entirely in some versions.

This operating range may be visually communicated to the user via an indicator bar (110) of an indicator (104) shown against a scale (130), described briefly above. At the distal end of indicator bracket (140) is a distally projecting indicator arm (146) which terminates at a laterally projecting finger (148) for controlling the movement of indicator (104). Indicator arm (146) and finger (148), best shown in FIG. 5, are configured to engage a tab (106) of indicator (104) such that indicator (104) is pivoted when indicator bracket (140) is actuated longitudinally. In the present example, indicator (104) is pivotably coupled to body (72) at a first end of indicator (104), though this is merely optional and other pivot points for indicator (104) will be apparent to one of ordinary skill in the art in view of the teachings herein. An indicator bar (110) is positioned on the second end of indicator (104) such that indicator bar (110) moves in response to the actuation of indicator bracket (140). Accordingly, as discussed above, indicator bar (110) is displayed through an indicator window (120) against a scale (130) (shown in FIG. 6) to show the relative gap distance d between anvil (40) and stapling head assembly (20).

Of course indicator bracket (140), indicator (104), and/or actuator handle assembly (70) may be further constructed in accordance with at least some of the teachings of U.S. Pat. No. 5,205,459; U.S. Pat. No. 5,271,544; U.S. Pat. No. 5,275,322; U.S. Pat. No. 5,285,945; U.S. Pat. No. 5,292,053; U.S. Pat. No. 5,333,773; U.S. Pat. No. 5,350,104; U.S. Pat. No. 5,533,661, the disclosures of which are incorporated by reference herein; and/or in accordance with other configurations as will be apparent to one of ordinary skill in the art in view of the teachings herein.

II. Exemplary Anvil Detection, Indicators, and Lock-Out Features

In some instances, it may be desirable for a user to detect when anvil (40) is sufficiently coupled to trocar (38). Such detection can confirm that anvil (40) is properly coupled to trocar (38) such that anvil (40) does not move distally relative to staple driver (24) when instrument (10) is fired. The indicator for such detection may be provided through a sensory indicator assembly (e.g., visual, auditory, tactile, etc.) and/or through a trigger lock-out assembly to prevent trigger (74) from being actuatable by the user. Accordingly, a user may be able to determine whether anvil (40) is properly attached, or fully seated on trocar (38), prior to firing instrument (10) or, in some instances, instrument (10) will prevent the user from firing until anvil (40) is properly attached. Accordingly, various anvil detection assemblies, indicator assemblies, and trigger lockout assemblies will now be described below.

A. Exemplary Anvil Presence Rod

Figure 7:
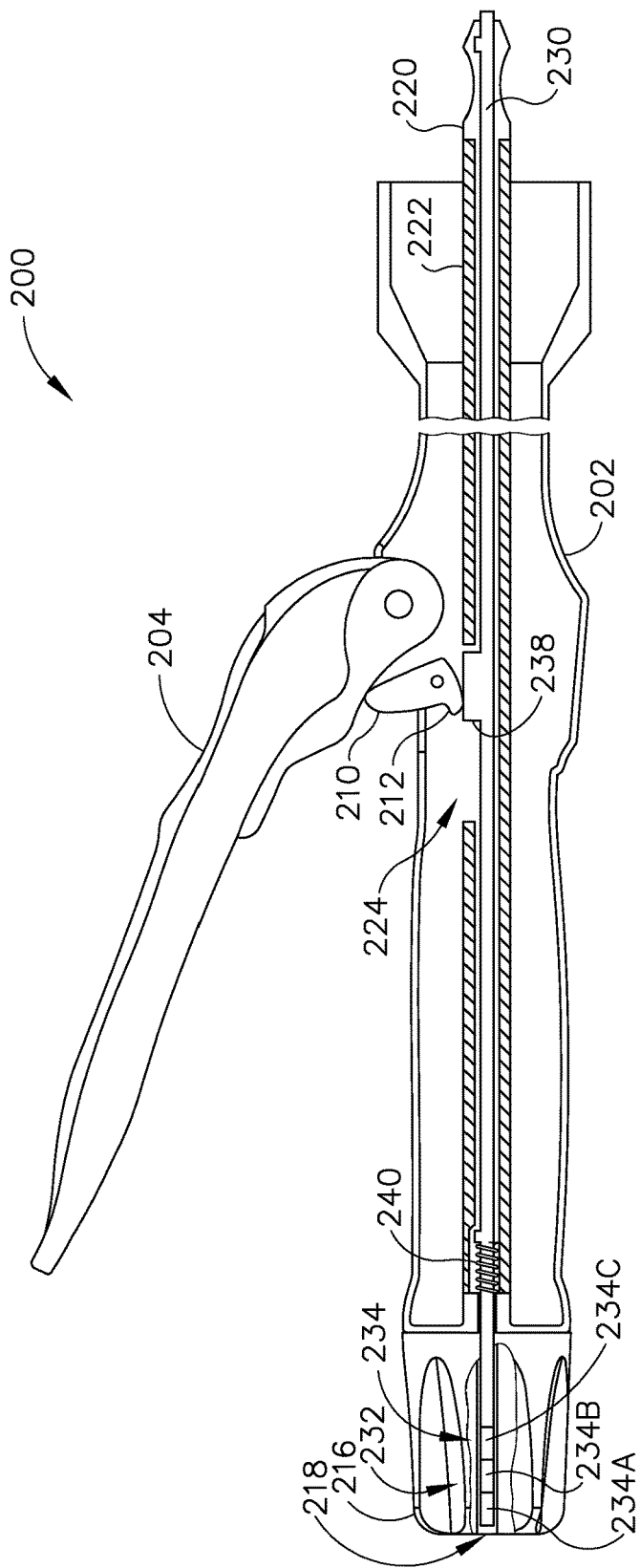
FIG. 7 depicts a partial side cross-sectional view of a surgical instrument having an exemplary trocar with an anvil presence rod.

FIG. 7 depicts a surgical instrument (200) that includes an exemplary anvil presence rod (230) incorporated into an exemplary trocar (220). In the present example, surgical instrument (200) comprises a body (202), a trigger (204), a lockout feature (210), an adjusting knob (216), a trocar (220), and an anvil presence rod (230). Body (202), trigger (204), lockout feature (210), adjusting knob (216), and trocar (220), may be constructed in substantial accordance with body (72), trigger (74), lockout feature (82), adjusting knob (98) and trocar (38) described above. Surgical instrument (200) may be further constructed substantially in accordance with surgical instrument (10) described above, or in accordance with at least some of the teachings of U.S. Pat. No. 5,205,459; U.S. Pat. No. 5,271,544; U.S. Pat. No. 5,275,322; U.S. Pat. No. 5,285,945; U.S. Pat. No. 5,292,053; U.S. Pat. No. 5,333,773; U.S. Pat. No. 5,350,104; and/or U.S. Pat. No. 5,533,661, the disclosures of which are incorporated by reference herein.

In the present example, trocar (220) includes a central rod tube (222) configured to slidably receive anvil presence rod (230) therein. Anvil presence rod (230) comprises a longitudinally stiff rod member that is slidable within rod tube (222) of trocar (220) and extends into an aperture (218) formed through adjusting knob (216). As shown in FIG. 7, anvil presence rod (230) is positioned in an unactuated position. Anvil presence rod (230) is slid proximally relative to trocar (220) when an anvil, such as anvil (40) shown in FIGS. 1-6, is inserted onto trocar (220), thereby moving anvil presence rod (230) proximally to an actuated position. This proximal movement of anvil presence rod (230) can be used to mechanically interact or release components of instrument (200) to indicate when the anvil is properly seated on trocar (220).

In the present example, anvil presence rod (230) includes a proximal end (232) that extends out through an aperture (218) formed in adjusting knob (216) when anvil presence rod (230) is slid proximally relative to trocar (220). This proximal end (232) may include one or more regions and/or markings (234) to visually indicate the position of anvil presence rod (230). By way of example only, such markings (234) may include a plurality of colors (e.g., red, yellow, green) and/or symbols (e.g., numbers, letters, etc.) to indicate the longitudinal position of anvil presence rod (230). In the example shown, markings (234) comprise three regions (234A, 234B, 234C) corresponding to the colors red (234A), yellow (234B), and green (234C). The user may use markings (234) to detect whether anvil presence rod (230) has been sufficiently actuated to indicate that the anvil is properly seated on trocar (220). For instance, the green marking portion (234C) may correspond to when the anvil has sufficiently coupled to trocar (220) such that the anvil will not detach when firing instrument (200). The yellow marking portion (234B) of the present example may be provided to indicate to the user that anvil presence rod (230) has been actuated proximally relative to trocar (220), but the anvil has not fully seated on trocar (220). In one alternative, only a single marking, such as green portion (234C), may be provided to indicate the position corresponding to when the anvil has sufficiently coupled to trocar (220). Of course it should be understood that markings (234) and/or the extension of proximal end (232) out of aperture (218) of adjusting knob (216) are merely optional.

In addition, anvil presence rod (230) of the present example is biased distally by a coil spring (240) that is disposed within a portion of trocar (220). Accordingly, when no object is actuating anvil presence rod (230) proximally relative to trocar (220), coil spring (240) urges the distal end of anvil presence rod (230) out of the distal end of rod tube (222). If a user attempts to couple the anvil to trocar (220) and the anvil is not properly seated on trocar (220), the distal bias provided by coil spring (240) ejects the anvil away from trocar (220). Thus, anvil presence rod (230) may physically and visually provide an indication to the user that the anvil is not properly seated on trocar (220). To provide the distal bias to anvil presence rod (230), coil spring (240) is coupled to a portion of anvil presence rod (230) such as by abutting a tab, being fixedly coupled at one end, and/or otherwise. In some versions, proximal end (232) of anvil presence rod (230) may not extend through aperture (218) of adjusting knob (216), but instead abuts coil spring (240) to provide the distal bias. A distal tab or flared portion (236), shown in FIG. 7, prevents anvil presence rod (230) from ejecting distally out of trocar (220) from the distal bias provided by coil spring (240), though this is also merely optional.

While a visual indicator may be provided by proximal end (232) and/or markings (234), in some versions, a feature may be desired that substantially prevents trigger (204) from being actuated by the user until the anvil is properly seated on trocar (220). In the present example, lockout feature (210) comprises a pivotable member having a leg (212) that abuts a protrusion (238) of anvil presence rod (230) when anvil presence rod (230) is in the unactuated position shown in FIG. 7. Protrusion (238) extends outwardly through a slot (224) formed in trocar (220) such that protrusion (238) is longitudinally slidable along slot (224) when anvil presence rod (230) is actuated proximally relative to trocar (220). The longitudinal length of protrusion (238) of the present example corresponds to the longitudinal distance traveled by anvil presence rod (230) to indicate that the anvil is properly coupled to trocar (220). Accordingly, when the anvil is properly coupled, protrusion (238) no longer abuts leg (212) of lockout feature (210). The user then pivots lockout feature (210) to unlock and permit operation of trigger (204) to fire instrument (200). The combination of protrusion (238) and lockout feature (210) may substantially prevent the user from firing instrument (10) when the anvil is not properly coupled to trocar (220). In some versions, leg (212) may be integrally formed with or otherwise linked to trigger (204). In some such versions, lockout feature (210) may be omitted. Of course other assemblies to prevent lockout feature (210) from pivoting prior to actuation of anvil presence rod (230) to the actuated position will be apparent to one of ordinary skill in the art in view of the teachings herein.

B. Exemplary Resiliently Biased Anvil Detection Features

Figure 8:
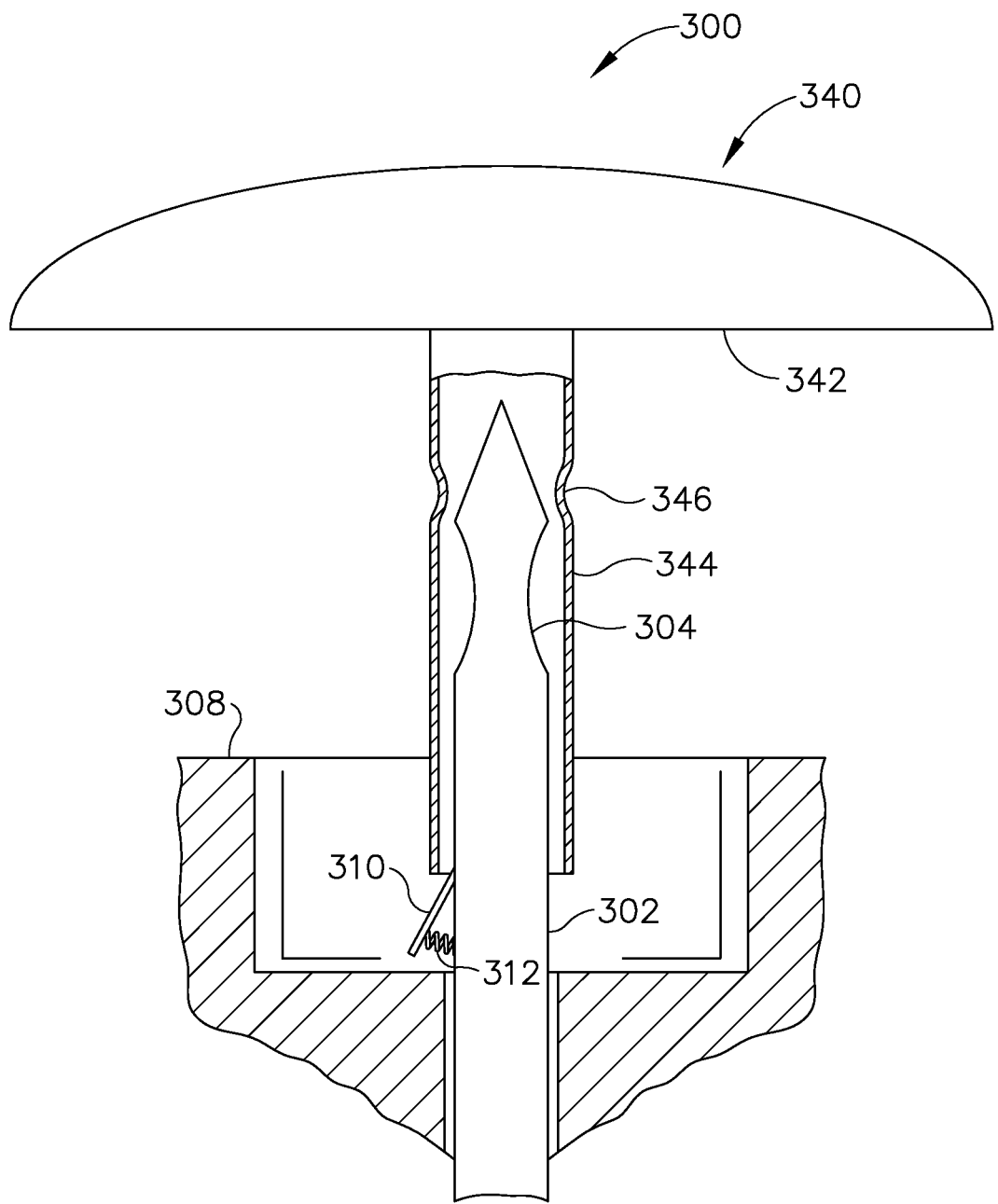
FIG. 8 depicts an enlarged partial cross-sectional view of an exemplary anvil detection assembly having a resiliently biased tab, an exemplary staple driver, a trocar, and an anvil.

FIG. 8 depicts an alternative anvil detection assembly (300) that may be incorporated into a surgical instrument, such as surgical instruments (10, 200) described above. In the example shown, anvil detection assembly (300) comprises a hinged tab (310) extending outwardly from a trocar (302). Trocar (302) may be constructed in accordance with at least some of the teachings of trocars (38, 220) described above. As shown in the present example, a spring (312) biases tab (310) outwardly from trocar (302), though this is merely optional. For instance, in one alternative, spring (312) may be omitted and tab (310) may be integrally formed with trocar (302) such that tab (310) is a resiliently biased tab. In addition, while a single tab (310) is illustrated, it should be understood that a plurality of tabs (310) may be positioned about trocar (302). When tab (310) is extended away from trocar (302), tab (310) of the present example mechanically interferes with a staple driver (308) to substantially prevent staple driver (308) from actuating distally relative to trocar (302). Accordingly, a user may be prevented from firing staple driver (308) via operation of a trigger, such as trigger (74) described above, until tab (310) is depressed against or into trocar (302).

In the example shown, an anvil (340) comprises an anvil head (342) and a hollow shaft (344). Anvil (340) may be further constructed in accordance with at least some of the teachings of anvil (40) described above. Hollow shaft (344) comprises a cylindrical tube configured to slide over trocar (302) and selectively couple anvil (340) to trocar (302). In the example shown, hollow shaft (344) includes detents (346) that engage indentations (304) of trocar (302) to selectively secure anvil (340) to trocar (302). Of course other coupling assemblies for selectively coupling anvil (340) to trocar (302) will be apparent to one of ordinary skill in the art in view of the teachings herein. When hollow shaft (344) is slid over trocar (302), hollow shaft (344) compresses tab (310) against trocar (302), thereby permitting staple driver (308) to actuate distally relative to trocar (302) and/or anvil (340) when the user operates the instrument. In the example shown, the length of hollow shaft (344) is such that hollow shaft (344) only engages tab (310) when anvil (340) is fully seated on trocar (302). The present assembly may thus prevent a user from firing the device unless anvil (340) is properly coupled to trocar (302). Of course still further configurations for anvil (340), tab (310), and/or trocar (302) will be apparent to one of ordinary skill in the art in view of the teachings herein.

In addition, or in the alternative, tab (310) may be mechanically associated with a lockout feature in the actuator handle assembly. By way of example only, tab (310) may comprise a camming surface that is operable to actuate a rod, such as anvil presence rod (230) described above, when tab (310) is compressed against trocar (302). The rod of this example may include a protrusion, such as protrusion (238), that selectively interferes with the release of a lockout feature depending upon the longitudinal position of the rod. In addition, or in the alternative, the rod may include a proximal end, such as proximal end (232), that protrudes out of the proximal end of the surgical instrument to provide visual feedback to the user. Of course tab (310) may be mechanically associated with other lockout features and/or visual indicators as will be apparent to one of ordinary skill in the art in view of the teachings herein. In another alternative, tab (310) may be positioned such that trocar (302) cannot be actuated proximally relative to staple driver (308) from an extended position via the adjusting knob. For instance, tab (310) may be positioned to abut staple driver (308) while trocar (302) is in the extended position. Accordingly, if the user attempts to actuate trocar (302) proximally via the adjusting knob, tab (310) resists the proximal actuation and provides tactile feedback that tab (310) has not been depressed by attachment of shaft (344) of anvil (340). If trocar (302) is not actuatable proximally due to the interference of tab (310), then, in an instrument such as instrument (10), a user may not pivot lockout feature (82) to release trigger (74) due to the position of indicator bracket (140), as discussed above. Thus, when tab (310) is extended, a user may be substantially prevented from firing the instrument. Of course still further configurations and assemblies incorporating tab (310) will be apparent to one of ordinary skill in the art in view of the teachings herein.

Figure 9B:
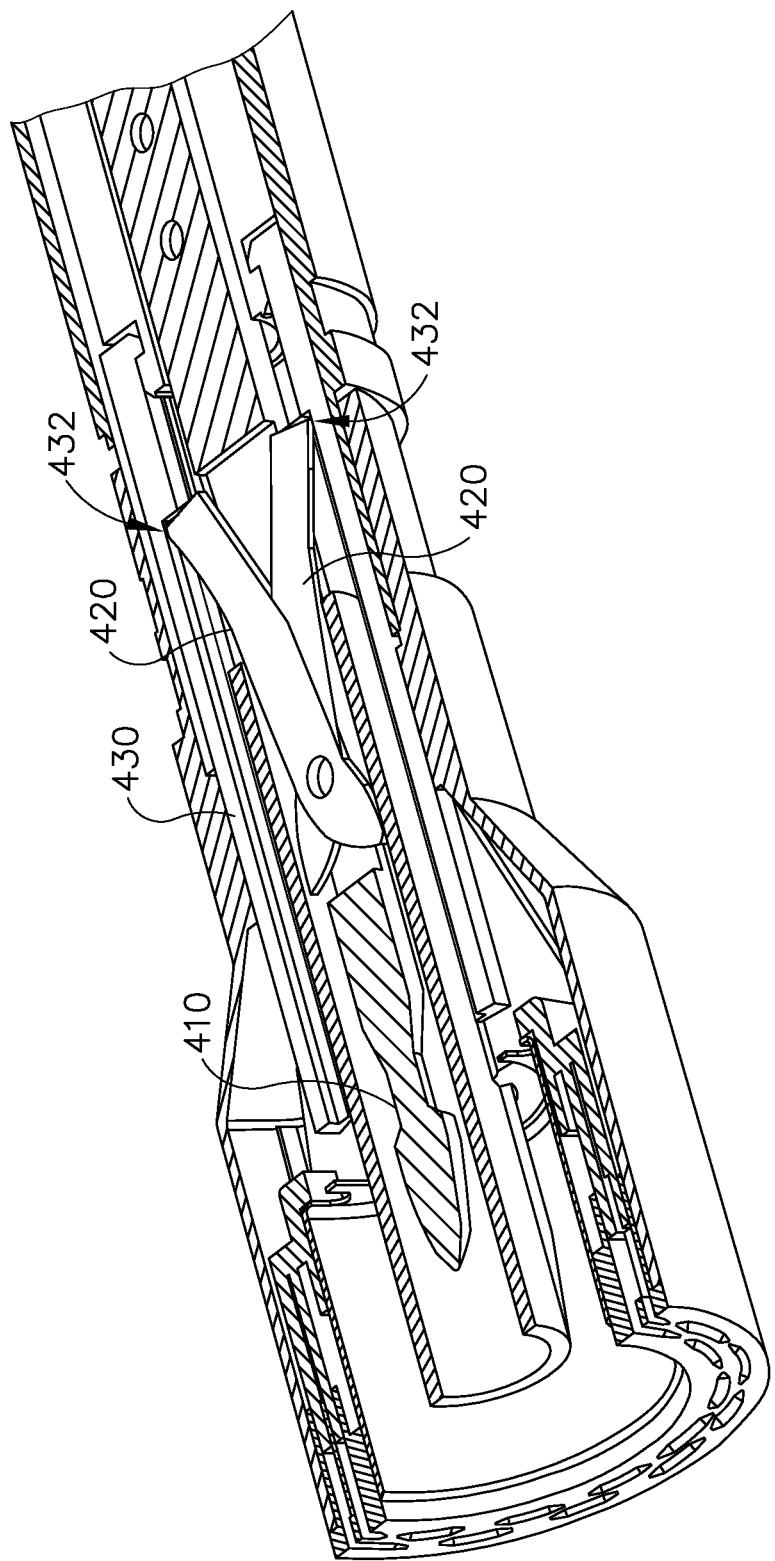
FIG. 9B depicts a partial cross-sectional view on the anvil detection assembly of FIG. 9A showing the trocar and spring clips in the retracted position without an anvil attached.
Figure 9C:
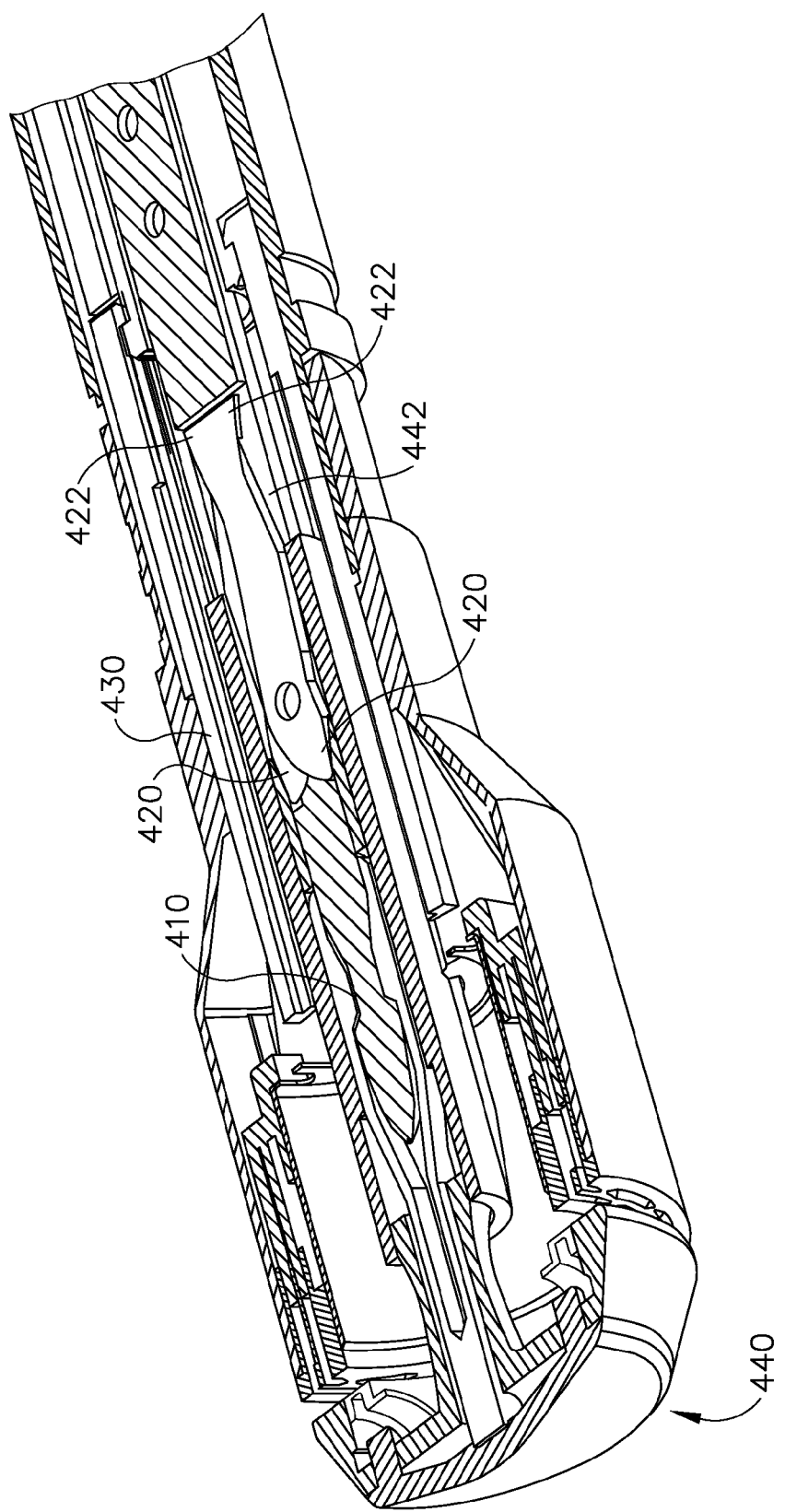
FIG. 9C depicts a partial cross-sectional view on the anvil detection assembly shown in the retracted position with the anvil attached.

FIGS. 9A-9C depict an alternative anvil detection assembly (400) comprising a trocar (410) having a pair of spring clips (420). In the example shown, spring clips (420) are contained within a slot (412) formed in trocar (410). As shown in FIG. 9A, spring clips (420) are biased outwardly from trocar (410) such that proximal ends (422) extend laterally from trocar (410). By way of example only, spring clips (420) are coupled to trocar (410) at a pivot point (424) and a spring (not shown) is interposed between spring clips (420) to bias each away from the other. In addition, or in the alternative, spring clips (420) may comprise resiliently biased members that are biased away from pivot point (424). In the example shown in FIG. 9A, when spring clips (420) are extended laterally, trocar (410) is prevent from actuating proximally due to proximal ends (422) engaging a trocar opening (416). Accordingly, if an anvil (440) (shown in FIG. 9C) is not coupled to trocar (410), then trocar (410) is prevented from actuating proximally relative to a staple driver (430). If a user desires to actuate trocar (410) proximally relative to staple driver (430) without anvil (440) attached, the user must squeeze spring clips (420) together to permit retraction.

As shown in FIG. 9B, when an anvil (440) (shown in FIG. 9C) is not coupled to trocar (410) and trocar (410) is retracted proximally relative to staple driver (430), spring clips (420) engage notches (432) formed in staple driver (430). As will be apparent to one of ordinary skill in the art in view of the teachings herein, spring clips (420) inserted into notches (432) substantially prevent staple driver (430) from actuating distally relative to trocar (410). Accordingly, if anvil (440) is not coupled to trocar (410), then spring clips (420) provide a lockout mechanism to prevent the instrument from firing. Finally, as shown in FIG. 9C, when anvil (440) is coupled to trocar (410), an anvil shaft (442) cams spring clips (420) inwardly such that proximal ends (422) do not engage notches (432). Accordingly, staple driver (430) can be actuated distally relative to trocar (410) to fire the instrument. Still further configurations for anvil detection assembly (400) and/or spring clips (420) will be apparent to one of ordinary skill in the art in view of the teachings herein.

C. Exemplary Magnetic Anvil Detection Assembly

Figure 10A:
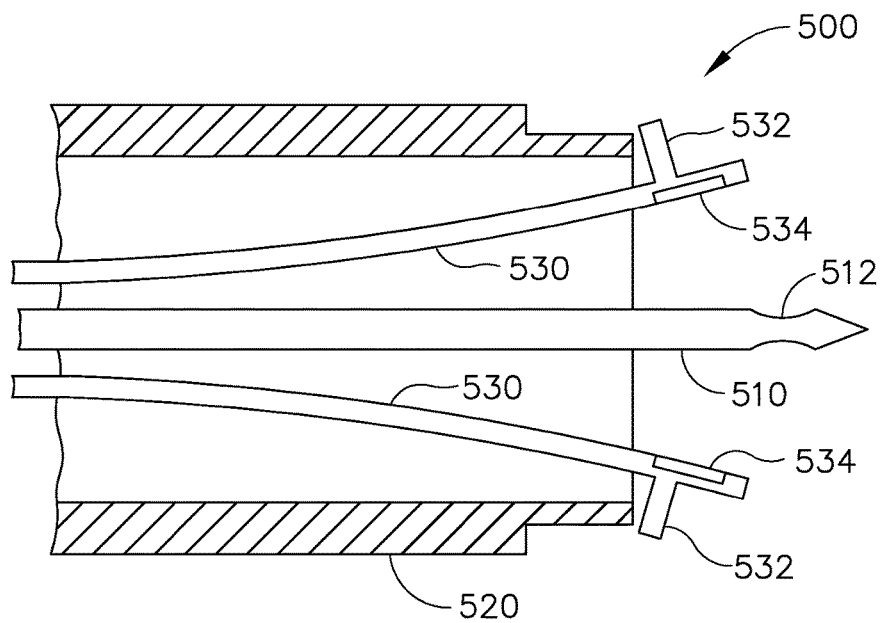
FIG. 10A depicts an enlarged partial longitudinal cross-sectional view of an anvil detection assembly having a pair of resiliently biased locking features with magnetic portions.
Figure 10B:
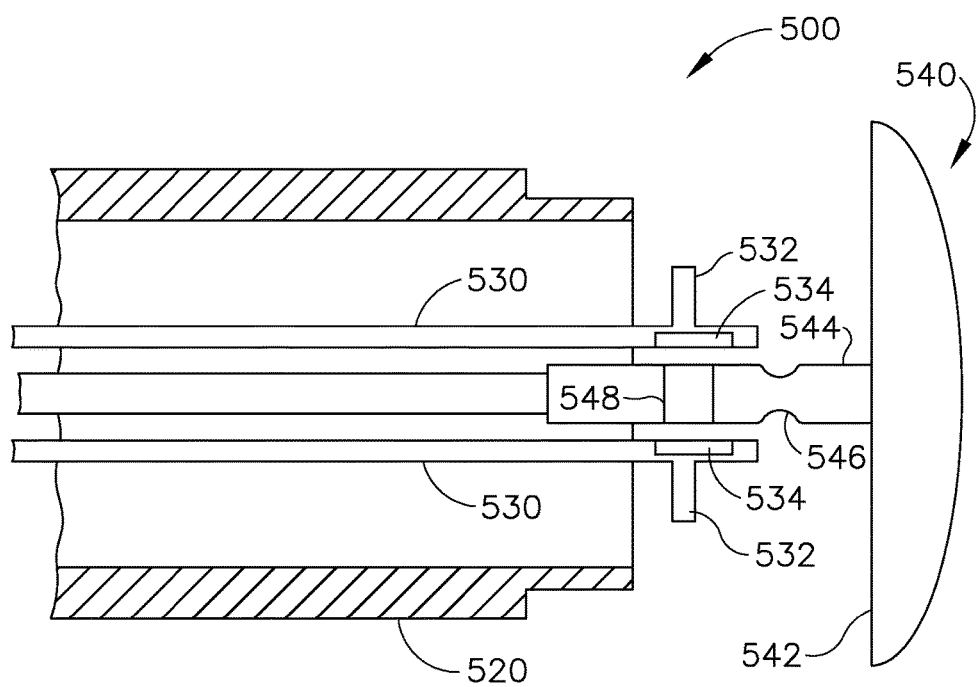
FIG. 10B depicts an enlarged partial longitudinal cross-sectional view of the anvil detection assembly of FIG. 10A showing a complementary anvil coupled to the trocar and aligned with the magnetic portions.

FIGS. 10A-10B depict an alternative anvil detection assembly (500) that may be incorporated into a surgical instrument, such as surgical instrument (10) described above. Referring initially to FIG. 10A, a trocar (510) and a staple driver (520) extend distally from an actuator handle assembly (not shown). Trocar (510) and staple driver (520) may be constructed in accordance with at least some of the teachings of trocar (38) and staple driver (24) described herein. A pair of resilient members (530) also extend distally from the actuator handle assembly and are biased outwardly away from trocar (510). The proximal ends (not shown) of resilient members (530) are coupled to a portion of the actuator handle assembly to mechanically ground resilient members (530). For instance, resilient members (530) may be integrally formed with the body of actuator handle assembly or mechanically coupled via an attachment member, such as a screw, bolt, adhesive, etc. In some versions, the proximal ends of resilient members (530) may be coupled to trocar (510). In another version, the proximal ends of resilient members (530) may be coupled to staple driver (520). Of course still further configurations to couple resilient members (530) at their proximal ends will be apparent to one of ordinary skill in the art in view of the teachings herein.

Resilient members (530) each comprise an elongated member having a lockout arm (532) and a magnet (534). Magnet (534) may be a ferrous magnet, a neodymium magnet, a samarium-cobalt magnet, or any other suitable magnet (534) as will be apparent to one of ordinary skill in the art in view of the teachings herein. Each lockout arm (532) extends outward from the longitudinal axis of a corresponding resilient member (530). In the example shown, each lockout arm (532) is perpendicular to the longitudinal axis of the corresponding resilient member (530) such that each lockout arm (532) is configured to mechanically interfere with the distal actuation of staple driver (520) relative to resilient member (530) and/or trocar (510). Accordingly, when resilient arms (530) are in a locked position, such as that shown in FIG. 10A, staple driver (520) is substantially prevented from actuating distally by lockout arms (532). While only a pair of resilient members (530) are shown, it should be understood that any number of resilient members (530) may be used to restrict distal actuation of staple driver (520). For example, 1, 2, 3, 4, 5, or 6 resilient members (530) may be disposed about trocar (510) and configured to interfere with the distal actuation of staple driver (520).

FIG. 10B depicts a complementary anvil (540) for anvil detection assembly (500). Anvil (540) comprises an anvil head (542) and a shaft (544). Anvil (540) may be further constructed in accordance with at least some of the teachings of anvil (40) described herein. Shaft (544) of the present example is configured to selectively couple anvil (540) to trocar (510). By way of example only, shaft (544) may comprise detents (546) configured to engage with indentations (512) (shown in FIG. 10A) of trocar (510) to selectively couple anvil (540) to trocar (510). Shaft (544) further comprises a magnetic portion (548) positioned along the longitudinal length of shaft (544). Magnetic portion (548) may comprise a single annular magnet embedded in shaft (544) or a plurality of magnets disposed within shaft (544). In addition, or in the alternative, magnetic portion (548) may not be embedded within shaft (544) but may be coupled to the exterior or interior surface of shaft (544). Furthermore, magnetic portion (548) may comprise one or more ferrous magnets, neodymium magnets, samarium-cobalt magnets, and/or any other suitable magnet as will be apparent to one of ordinary skill in the art in view of the teachings herein. In the present example, magnetic portion (548) is longitudinally positioned to align with magnets (534) of resilient arms (530) only when anvil (540) is fully seated on trocar (510).

As shown in FIG. 10B, when anvil (540) is fully seated, magnetic portion (548) attracts magnets (534) such that resilient arms (530) bend inwardly towards shaft (544) and/or trocar (510). Accordingly, lockout arms (532) no longer mechanically interfere with staple driver (520), thereby permitting staple driver (520) to actuate longitudinally to allow the user to fire the instrument. In one merely exemplary alternative, resilient arms (530) may omit magnets (534) and may instead be constructed of a ferrous material such that magnetic portion (548) attracts resilient arms (530) inwardly. In this configuration, the spring constant for resilient arms (530) may be set such that lockout arms (532) no longer impede distal movement of staple driver (520) only when anvil (540) is fully seated on trocar (510). By way of example only, as anvil (540) is attached to trocar (510), resilient arms (530) begin to bend inwardly due to magnetic portion (548) magnetically attracting the material. Only when anvil (540) is seated fully on trocar (510) does the attractive force from magnetic portion (548) on resilient arms (530) displace resilient arms (530) such that lockout arms (532) no longer impede the longitudinal actuation of staple driver (520). In some versions, resilient arms (530) may comprise magnets (534) while magnetic portion (548) of shaft (544) is omitted. Of course still further configurations for anvil detection assembly (500) will be apparent to one of ordinary skill in the art in view of the teachings herein.

D. Exemplary Outer Shaft Anvil Detection Feature

Figure 11:
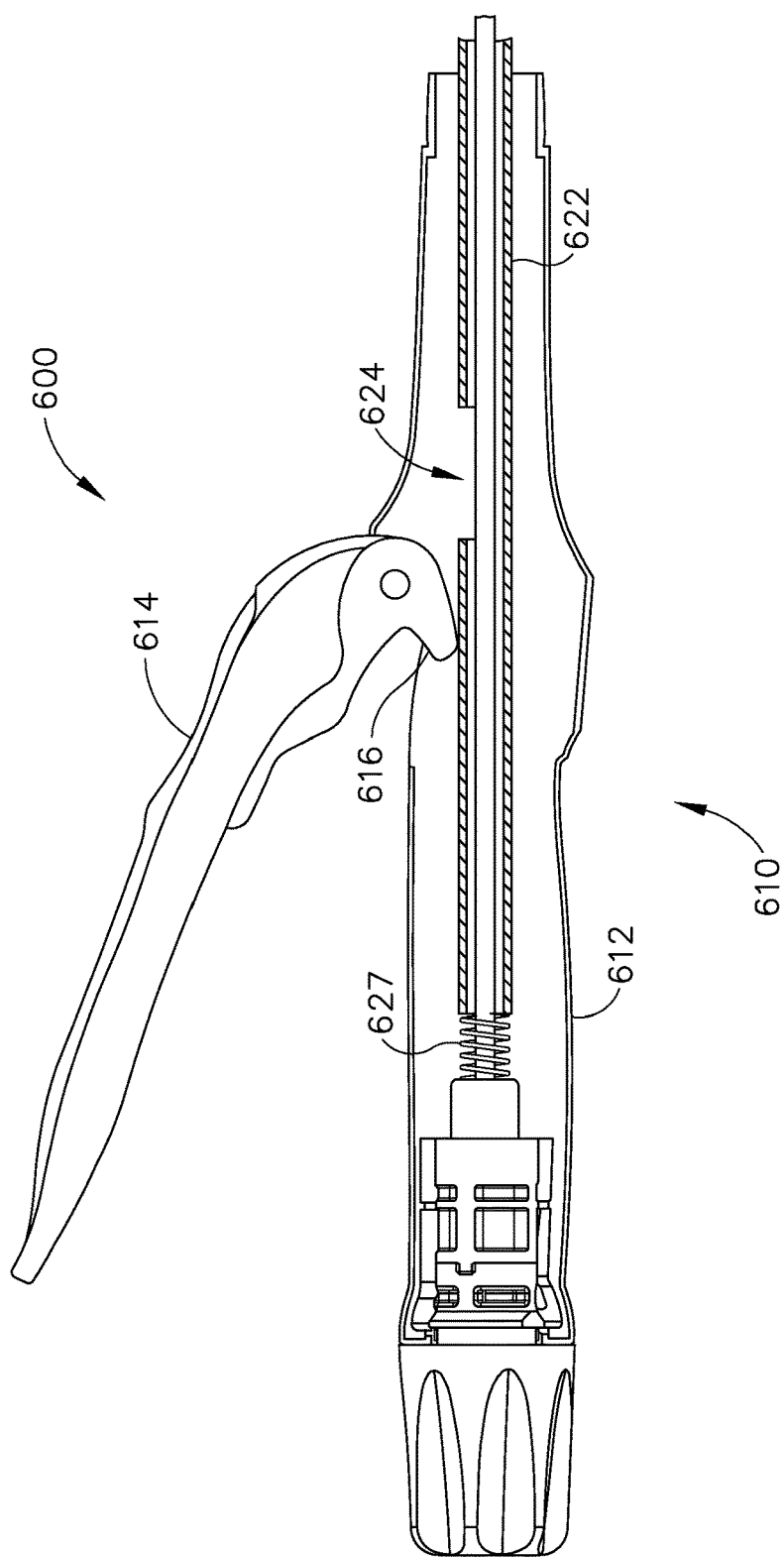
FIG. 11 depicts a side cross-sectional view of an exemplary surgical instrument having an exemplary anvil detection assembly with an anvil sensing tube.
Figure 12:
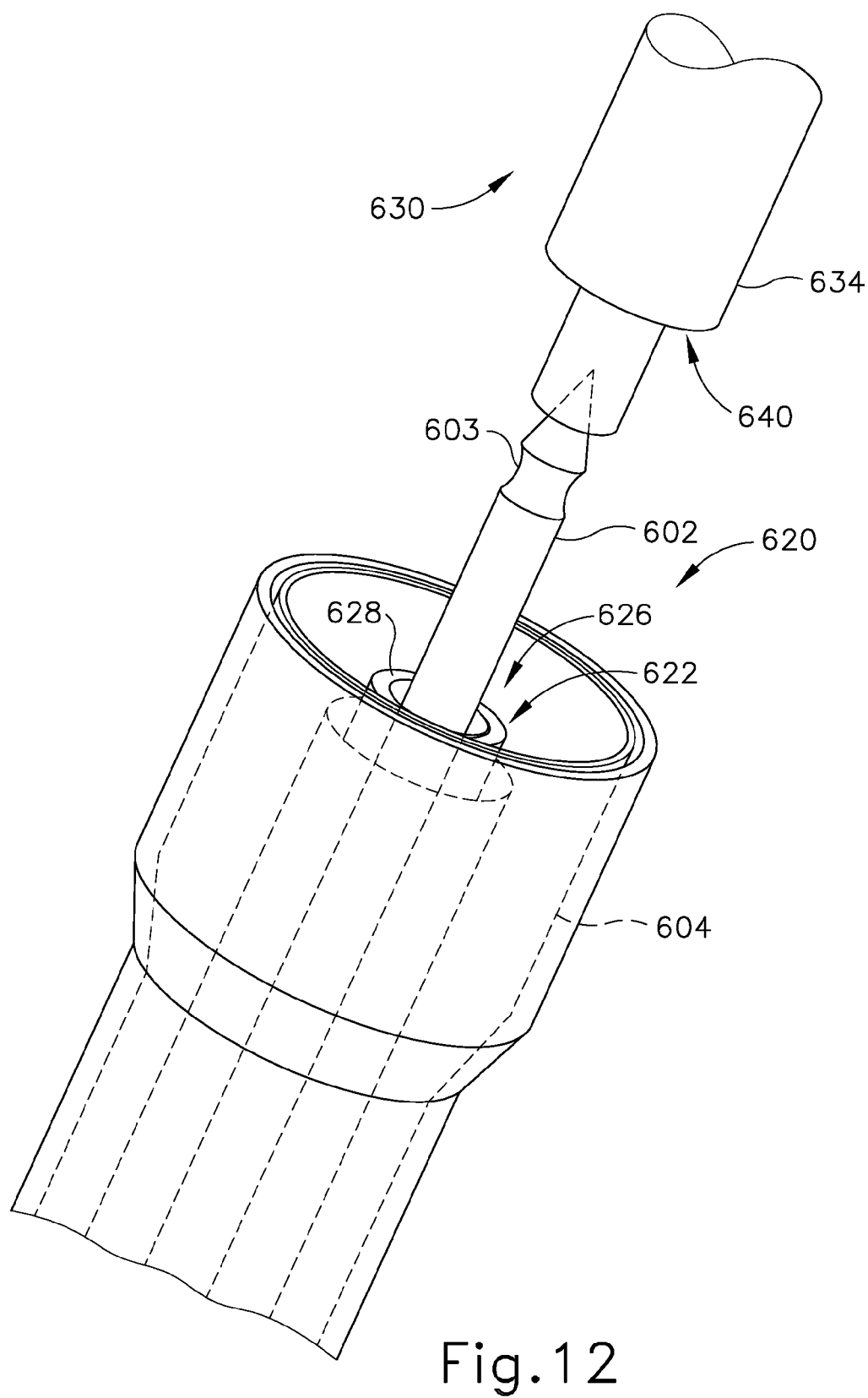
FIG. 12 depicts an enlarged partial perspective view of the distal end of the anvil detection assembly of FIG. 11.

FIGS. 11-12 depicts yet another anvil detection assembly (620) for a surgical instrument (600) comprising an anvil sensing tube (622) slidably disposed about a trocar (602). As shown in FIG. 11, anvil sensing tube (620) extends proximally into an actuator handle assembly (610). Actuator handle assembly (610) of the present example includes a trigger (614) pivotable relative to a body (612). Trigger (614) includes an arm or feature (616) extending outwardly from a pivot point of trigger (614) such that arm (616) is pivoted with trigger (614). In some versions, a pair of arms (616) may be provided, such as trigger arms (76) described above. Alternatively, or in addition, arm (616) may be a separate feature that distinct from trigger arms (76). Instrument (600), trocar (602), and/or actuator handle assembly (610) may be further constructed in accordance with at least some of the teachings for instrument (10), trocar (38), and/or actuator handle assembly (70) described above.

Anvil sensing tube (622) of the present example comprises a tubular member coaxially disposed about trocar (602), though it should be understood that this is merely optional. In some versions, anvil sensing tube (622) may comprise a longitudinal bar extending along a side of trocar (602) or anvil sensing tube (622) may include a U-shaped member partially encircling a portion of trocar (602). Still further configurations for anvil sensing tube (622) will be apparent to one of ordinary skill in the art in view of the teachings herein. Anvil sensing tube (622) shown in FIG. 11 includes a notch (624) formed in a proximal portion of anvil sensing tube (622). Accordingly, when anvil sensing tube (622) is in an unactuated position, such as that shown in FIG. 11, notch (624) is not aligned with arm (616). Instead, arm (616) abuts a portion of anvil sensing tube (622) such that trigger (614) cannot be pivoted relative to body (612). When anvil sensing tube (622) is actuated proximally relative to trocar (602) to an actuated position, as will be discussed in greater detail below, notch (624) is aligned with arm (616) such that trigger (614) is pivotable relative to body (612). A spring (627) is coupled to a proximal end of anvil sensing tube (622) to bias anvil sensing tube (622) distally relative to actuator handle assembly (610).

In the present example, the longitudinal position of notch (624) is located such that arm (616) aligns with notch (624) only when an anvil (630) is fully seated on trocar (602) and trocar (602) is actuated proximally into the "green zone" described above. The "green zone" indicates that the anvil gap, or the distance between the anvil head (not shown) and staple driver (604), is within a desired operating range. If anvil (630) is not fully seated on trocar (602), then spring (627) ejects anvil (630) off of trocar (602), as will be discussed in more detail below. If anvil (630) is fully seated on trocar (602) and notch (624) and arm (616) are aligned, the user can operate trigger (614) to fire instrument (600). Of course notch (624) may have other longitudinal positions on anvil sensing tube (622). Still further configurations for anvil sensing tube (622) and/or actuator handle assembly (610) will be apparent to one of ordinary skill in the art in view of the teachings herein.

Referring now to FIG. 12, anvil sensing tube (622) is shown disposed between trocar (602) and staple driver (604). Anvil sensing tube (622) includes a mating surface (628) at a distal end (626) that is configured to engage an annular shelf (640) of an anvil (630). Anvil (630) of the present example comprises an anvil head (not shown), a shaft (634), an annular shelf (640) formed on shaft (634), and a coupling feature (not shown). Anvil (630) may be further constructed in accordance with at least some of the teachings for anvil (40) described herein. When anvil (630) is pushed onto trocar (602), annular shelf (640) engages mating surface (628) to actuate anvil sensing tube (622) proximally relative to trocar (602) and/or staple driver (604). The coupling feature of anvil (630) selectively couples anvil (630) to trocar (602). By way of example only, the coupling feature may include detents (not shown) formed on shaft (634) that engage with indentations (603) of trocar (602). In the present example, if anvil (630) is fully seated on trocar (602) (i.e., selectively coupled together by the coupling feature), then spring (628) does not eject anvil (630). If anvil (630) is not fully seated on trocar (602) (i.e., the coupling feature did not engage and secure anvil (630) to trocar (602)), then spring (628) ejects anvil (630). While the ejection of anvil (630) of the present example occurs when anvil (630) is initially coupled to trocar (602), it should be understood that, in other versions, the ejection of anvil (630) may occur when trocar (602) is actuated proximally via the adjusting knob. In such an alternative version, annular shelf (640) engages mating surface (628) when trocar (602) is actuated proximally via the rotating knob. Of course still further configurations for anvil (630) and/or anvil sensing tube (622) will be apparent to one of ordinary skill in the art in view of the teachings herein.

In the present example, notch (624) does not align with arm (616) until trocar (602) and anvil (630) are actuated proximally into the "green zone" described above. In this version, trigger (614) is "locked" until anvil (630) is both fully seated and positioned in the "green zone." In other versions, notch (624) may align with arm (616) of trigger (614) when anvil (630) is initially fully seated on trocar (602). In this version, the user may partially pivot trigger (614) to determine that anvil (630) is fully seated on trocar (602) prior to actuating trocar (602) and anvil (630) proximally via the rotating knob. Accordingly, the user may be provided with a form of tactile feedback indicating anvil (630) is fully seated on trocar (602). Of course still further versions of anvil sensing tube (622) and/or annular shelf (640) will be apparent to one of ordinary skill in the art in view of the teachings herein.

Figure 13:
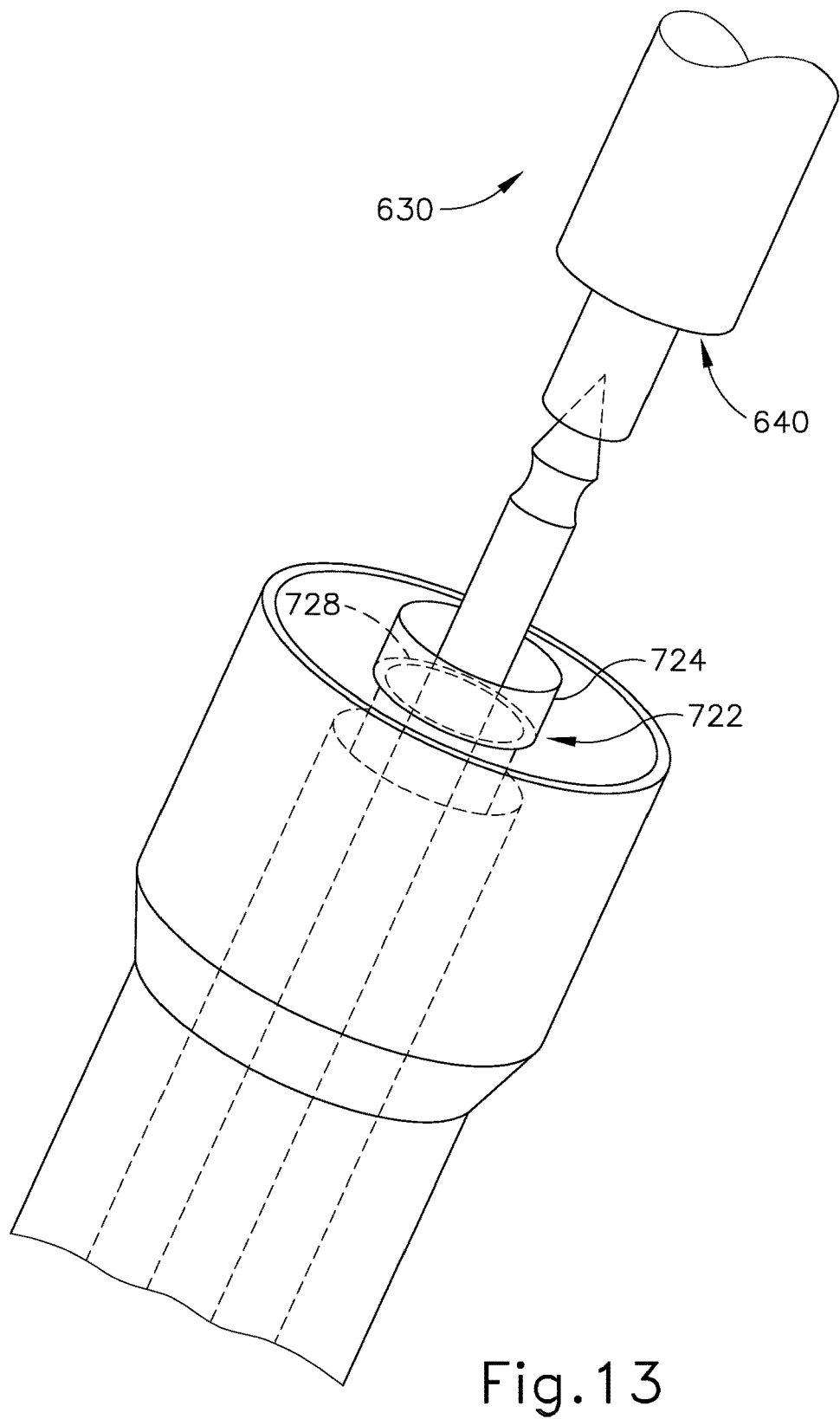
FIG. 13 depicts an enlarged partial perspective view of another exemplary anvil detection assembly having an exemplary alternative anvil presence tube with a cup.

For instance, in the example shown in FIG. 13, an alternative anvil sensing tube (722) is shown having a cup (724) configured to receive and guide annular shelf (640) of anvil (630) into engagement with mating surface (728) of anvil sensing tube (722). Anvil sensing tube (722) may be further constructed in accordance with anvil sensing tube (622) described above. Accordingly, when annular shaft (640) engages mating surface (728), anvil sensing tube (722) is configured to permit a trigger, such as trigger (614) to be operated to fire the instrument. While the example shown includes annular shelf (640), in other versions, cup (724) may be configured to mate with a shaft (634) that omits annular shelf (640).

Figure 14:
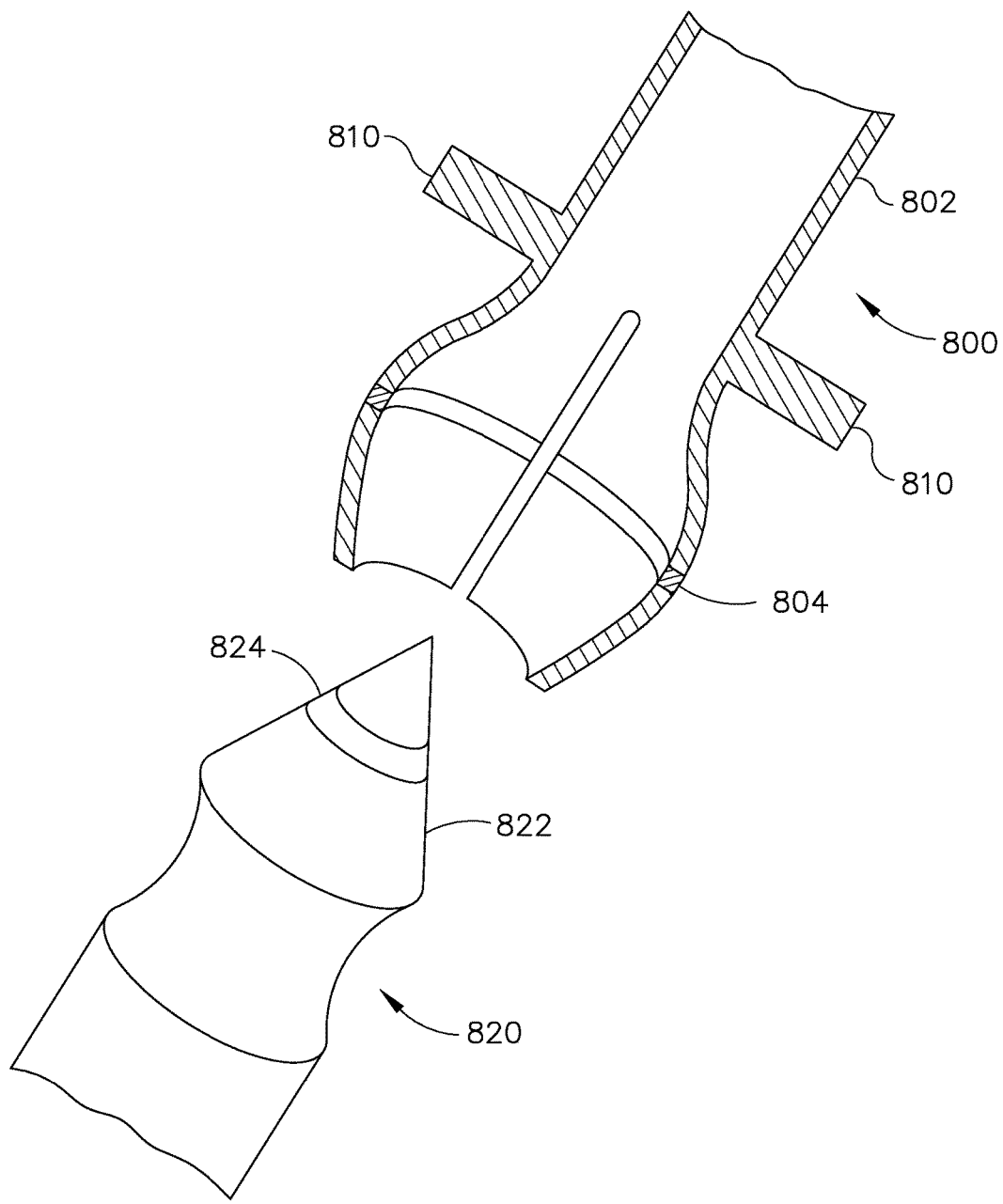
FIG. 14 depicts an enlarged partial cross-sectional view of yet another exemplary anvil detection assembly showing an exemplary alternative anvil with a split collet shaft and a pair of tabs.

FIG. 14 depicts an alternative anvil (800) that may be used to engage anvil sensing tubes (622, 722). Anvil (800) comprises an anvil head (not shown), a shaft (802), and a pair of pegs (810) extending outwardly from shaft (802). Shaft (802) of the present example comprises a split collet configured to fit over and selectively couple to a flared portion (822) of a trocar (820). In some versions shaft (802) may comprise a magnetic member (804) to be magnetically guided towards trocar (820). In addition, or in the alternative, trocar (820) and/or flared portion (822) may comprise a magnetic member (824) to guide shaft (802) onto trocar (820). Pegs (810) are configured to engage mating surfaces (628, 728) in a substantially similar manner to annular shelf (640). Accordingly, when shaft (802) is coupled to trocar (820) and pegs (810) engage mating surface (628, 728), anvil (800) and trocar (820) can be actuated proximally via an adjusting knob such that anvil sensing tube (622, 722) engages and/or disengages a locking feature, such as arm (616) and notch (624) described above. In some versions, mating surfaces (628, 728) may include a recessed portion (not shown) such that pegs (810) snap into the recessed portion to selectively secure anvil (800) to anvil sensing tubes (622, 722).

Figure 15:
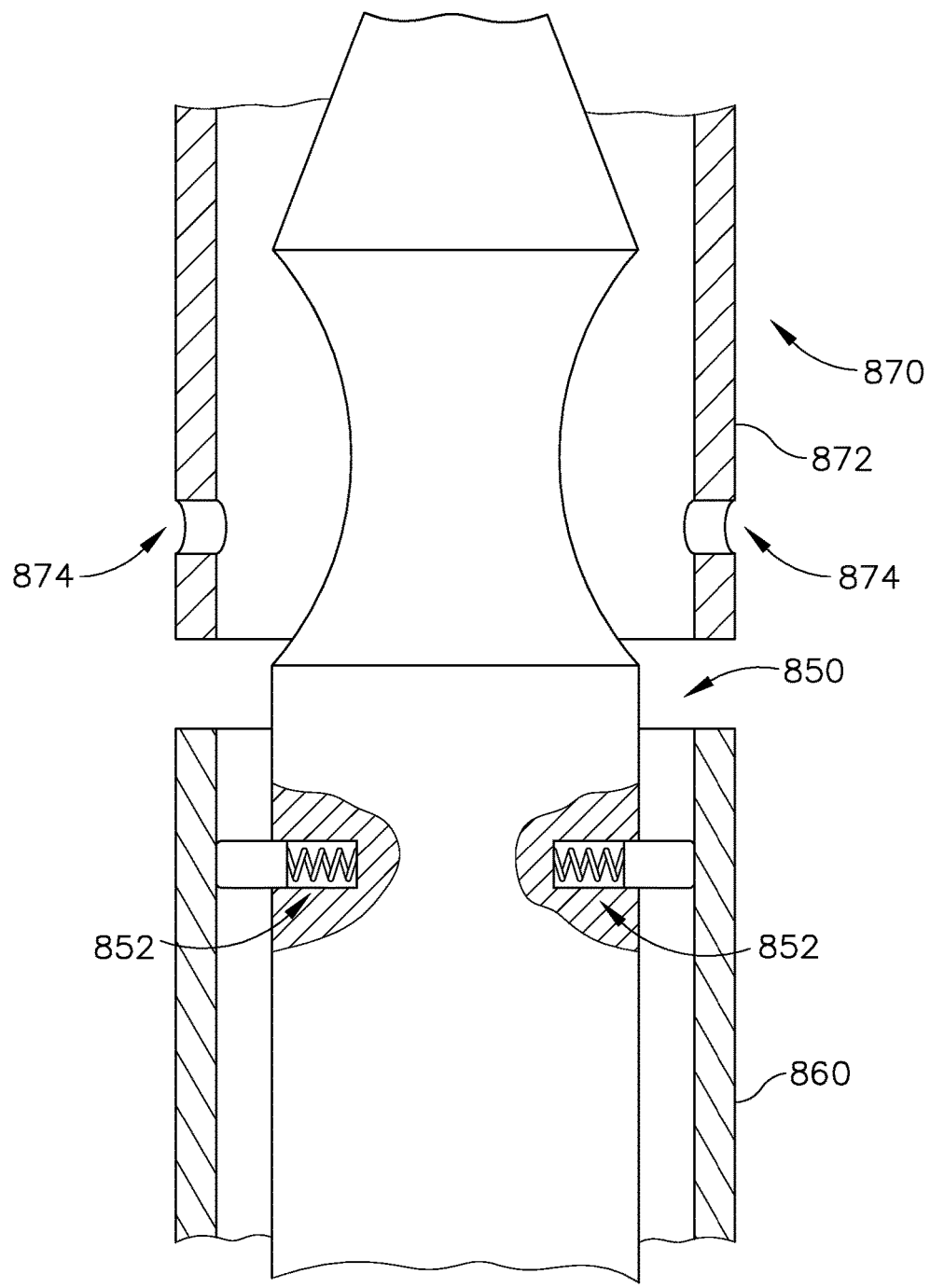
FIG. 15 depicts an enlarged partial cross-sectional view of a further exemplary anvil detection assembly showing a trocar with spring-loaded pins.

In yet a further version, FIG. 15 depicts an alternative trocar (850) having spring-loaded pins (852) biased outwardly against an anvil sensing tube (860). Anvil sensing tube (860) of the present example may be constructed in accordance with at least some of the teachings for anvil sensing tubes (622, 722) described above. Anvil (870) of the present example includes a shaft (872) that has a pair of openings (874) into which pins (852) spring into when shaft (872) is pushed onto trocar (850). Accordingly, when anvil (870) is inserted onto trocar (850), shaft (872) engages anvil sensing tube (860) and pushes anvil sensing tube (860) proximally relative to trocar (850). Once shaft (872) has actuated anvil sensing tube (860) proximally a predetermined distance, pins (852) spring into openings (874), thereby securing shaft (872) to trocar (850).

Of course still further configurations for anvils (630, 800, 870), anvil sensing tubes (622, 722), and/or trocars (602, 820, 850) will be apparent to one of ordinary skill in the art in view of the teachings herein.

E. Exemplary Lockout Features

While the foregoing examples have demonstrated various anvil detection assemblies, it may be preferable for the foregoing assemblies to engage one or more lockout features to release trigger (74) to fire instrument (10). For instance, in some versions it may be preferable for the anvil detection features to pop out a lockout button that must be depressed or operated by the user to release trigger (74), thereby preventing instrument (10) from being fired until anvil (40) is properly coupled to trocar (38) and the lockout button is operated by the user. Alternatively, it may be preferable for the anvil detection assembly to release an indicator and release lockout feature (82) such that the indicator visually indicates that anvil (40) is fully seated on trocar (38) and that the lockout feature can be disengaged to operate trigger (74). Accordingly, it should be understood that the following examples may be combined with one or more of the foregoing anvil detection assemblies and/or with any other anvil detection assembly as will be apparent to one of ordinary skill in the art in view of the teachings herein.

i. Exemplary Lockout Button Assembly Having a Three Position Button

Figures 16A, 16B:
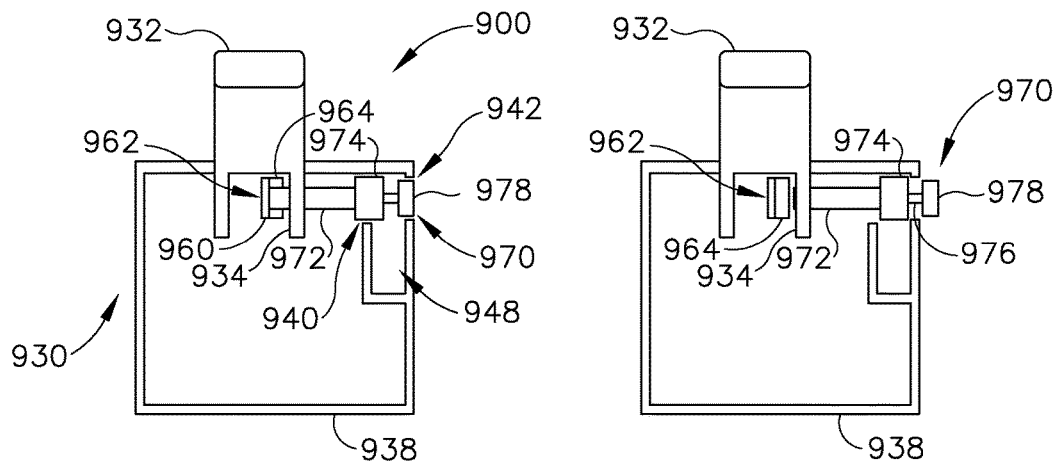
FIG. 16A depicts a rear cross-sectional view of an exemplary surgical instrument showing an exemplary lockout button assembly with a button shown in a first position.
FIG. 16B depicts a rear cross-sectional view of the surgical instrument of FIG. 16A showing the button cammed to a second position.
Figures 16C, 17:
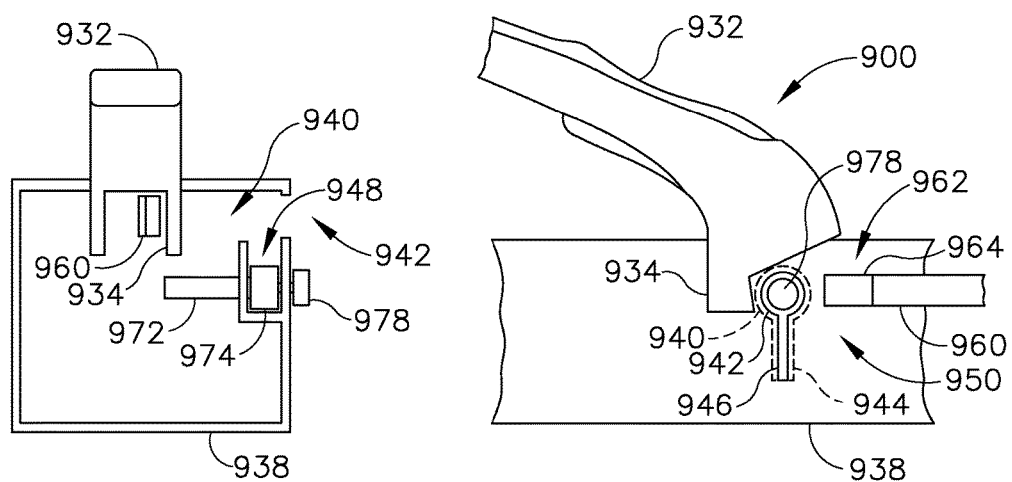
FIG. 16C depicts a rear cross-sectional view of the surgical instrument of FIG. 16A showing the button actuated to a third position.
FIG. 17 depicts a side elevation view of the surgical instrument of FIG. 16A with a portion of the body removed.

FIGS. 16A-17 depict an exemplary surgical instrument (900) having an exemplary lockout button assembly (950). Referring initially to FIG. 16A, lockout button assembly (950) comprises an anvil sensing shaft (960) extending longitudinally into actuator handle assembly (930) to engage a button (970). Anvil sensing shaft (960) includes a proximal end (962) having an obliquely angled camming surface (964) configured to engage button (970). Anvil sensing shaft (960) may be further constructed in accordance with the teachings for anvil sensing tube (622) described herein, though it should be understood that any of the foregoing anvil detecting assemblies may be used in addition or in the alternative to anvil sensing shaft (960). Actuator handle assembly (930) of the present example includes a body (938) having a first lateral hole (940) (shown in phantom in FIG. 17), a second lateral hole (942), a first channel (944) (shown in phantom in FIG. 17), a second channel (946), and a vertical slot (948). Button (970) comprises an inner member (972), an intermediate member (974), an intermediate axle (976), and an outer member (978). In the present example, first lateral hole (940) is sized to permit intermediate member (974) of button (970) to pass therethrough. Second lateral hole (942) is sized to permit outer member (978) to pass therethrough, but is sized to not permit intermediate member (974) therethrough. First channel (944) is configured to permit inner member (972) to actuate vertically along first channel (944). Second channel (946) is configured to permit intermediate axle (976) to actuate vertically along second channel (946). Finally, vertical slot (948) is configured to permit intermediate member (974) to actuate vertically therein. Of course still further configurations for button (970) and/or body (938) will be apparent to one of ordinary skill in the art in view of the teachings herein.

Referring to FIGS. 16A and 17, button (970) is initially positioned such that inner member (972) mechanically interferes with the actuation of trigger (932). In the example shown, button (970) is positioned such that a protrusion (934) extending from trigger (932) abuts inner member (972) to prevent a user from pivoting trigger (932). As shown in FIG. 16A, intermediate member (974) is within first lateral hole (940) and outer member (978) is within second lateral hole (942), thereby forming a substantially flush outer surface of body (938). When anvil sensing shaft (960) is actuated proximally via attachment of an anvil, such as anvil (40), camming surface (964) engages inner member (972) to cam button (970) outwardly, as shown in FIG. 16B. When button (970) is cammed outwardly, outer member (978) extends outward from second lateral hole (942), intermediate axle (976) substantially aligns with second channel (946), intermediate member (974) enters into vertical slot (948), and inner member (972) substantially aligns with first channel (944). As shown in FIG. 16B, outer member (978) provides visual indication (via protruding out of body (938)) that anvil sensing shaft (960) has been actuated proximally relative to actuator handle assembly (930) and that the anvil is fully seated on the trocar. In this position, inner member (972) still mechanically interferes with the actuation of trigger (932). In the present example, button (970) is actuated outwardly to the position shown in FIG. 16B by anvil sensing shaft (960) when the anvil is initially coupled to the trocar. Once the anvil is coupled, the user can reduce the anvil gap via an adjusting knob, such as adjusting knob (98) described above. Once the device is within the desired operating range, or "green zone," the user can actuate button (970) downwardly via sliding outer member (978) along the outer surface of body (938). In the present example, intermediate axle (976) slides within second channel (946), intermediate member (974) slides within vertical slot (948), and inner member (972) slides along first channel (944). Accordingly, as shown in FIG. 16C, inner member (972) is actuated to a position such that protrusion (934) of trigger (932) is no longer impeded by inner member (972). The user may then fire instrument (900). While the foregoing example has been described in reference to a vertical lockout button assembly (950) it should be understood that other orientations for assembly (950) may be used, such as longitudinal and/or any other angle. Furthermore, while the foregoing example has been described in reference to linear motion to describe actuating the lockout button assembly (950), it should be understood that other orientations for actuating the outer member (978) may be used, including rotation.

In some versions, button (970) is cammed via anvil sensing shaft (960) when the anvil and trocar are actuated proximally via the adjusting knob. In addition, or in the alternative, a lockout feature, such as lockout feature (82) described above, may be provided to lockout trigger (932) unless the anvil and trocar are within the "green zone," thereby providing a secondary lockout assembly. In yet a further configuration, inner member (972) may be configured such that when button (970) is cammed outwardly via anvil sensing shaft (960), inner member (972) no longer interferes with protrusion (934) of trigger (932). In this configuration, channels (944, 946), vertical slot (948), intermediate member (974) and/or intermediate axle (976) may be omitted. Further still, a spring (not shown) may be interposed between intermediate member (974) and/or inner member (972) and a portion of body (938) to bias button (970) inwardly such that button (970) is not actuated outwardly unless anvil sensing shaft (960) cams button (970) against the spring bias. The user may then fire instrument (900). Of course still further configurations for surgical instrument (900) and/or lockout button assembly (950) will be apparent to one of ordinary skill in the art in view of the teachings herein.

Figures 18A, 18B:
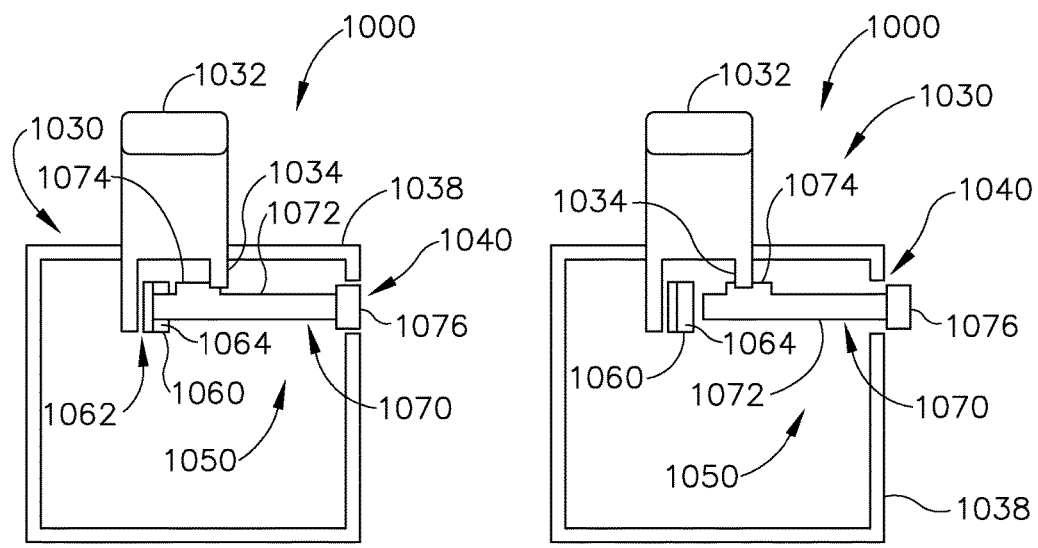
FIG. 18A depicts a rear cross-sectional view of an exemplary surgical instrument with an alternative exemplary lockout button assembly, with a button shown in a first position.
FIG. 18B depicts a rear cross-sectional view of the surgical instrument of FIG. 18A showing the button cammed to a second position.
Figure 18C:
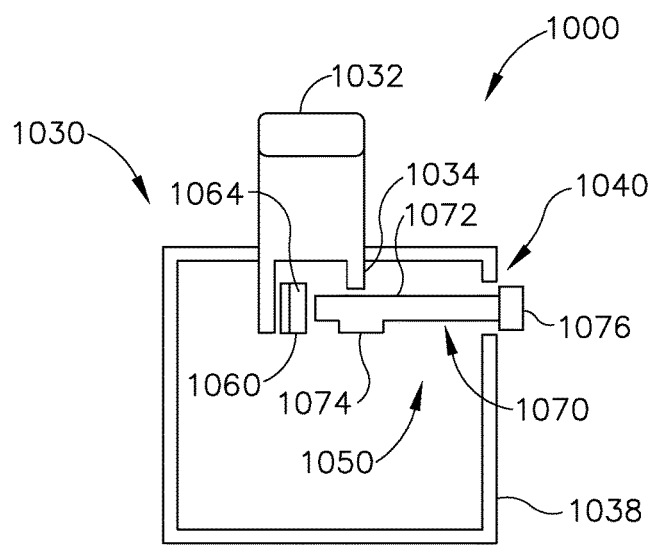
FIG. 18C depicts a rear cross-sectional view of the surgical instrument of FIG. 18A showing the button rotated to a third position.

By way of example only, FIGS. 18A-18C depict an exemplary surgical instrument (1000) having an exemplary lockout button assembly (1050). Referring initially to FIG. 18A, lockout button assembly (1050) comprises an anvil sensing shaft (1060) extending longitudinally into actuator handle assembly (1030) to engage a button (1070). Anvil sensing shaft (1060) includes a proximal end (1062) having an obliquely angled camming surface (1064) configured to engage button (1070). Anvil sensing shaft (1060) may be further constructed in accordance with the teachings for anvil sensing tube (622) described herein, though it should be understood that any of the foregoing anvil detecting assemblies may be used in addition or in the alternative to anvil sensing shaft (1060). Actuator handle assembly (1030) of the present example includes a body (1038) having a hole (1040). Button (1070) comprises an inner member (1072), a paddle feature (1074) on inner member (1072), and an outer member (1076). In the present example, hole (1040) is sized to permit outer member (1076) of button (1070) to pass therethrough. Of course further configurations for button (1070) and/or body (1038) will be apparent to one of ordinary skill in the art in view of the teachings herein.

Referring to FIG. 18A, button (1070) is initially positioned such that paddle feature (1074) mechanically interferes with the actuation of a trigger (1032). In the example shown, a protrusion (1034) extending from trigger (1032) abuts paddle feature (1074) to prevent a user from pivoting trigger (1032), though other features may be provided to prevent the user from pivoting trigger (1032). As shown in FIG. 18A, outer member (1076) is within hole (1040) of body (1038), such that outer member (1076) is substantially flush with the outer surface of body (1038). When anvil sensing shaft (1060) is actuated proximally via attachment of an anvil, such as anvil (40), camming surface (1064) engages inner member (1072) to cam button (1070) outwardly to a second position, as shown in FIG. 18B. When button (1070) is cammed outwardly, outer member (1076) extends outward from hole (1040). Outer member (1076) thus provides a visual indication (by protruding out of body (1038)) that anvil sensing shaft (1060) has been actuated proximally relative to actuator handle assembly (1030) and that the anvil is fully seated on the trocar. Once the anvil is coupled, the user can reduce the anvil gap via an adjusting knob, such as adjusting knob (98) described above. Paddle feature (1074) continues to prevent actuation of trigger (1032) at this stage. Once the anvil gap is within the desired operating range, or "green zone," the user rotates button (1070) via outer member (1076) to a third position. As shown in FIG. 18C, in one merely exemplary version, the user rotates button (1070) such that paddle feature (1074) is oriented approximately 180 degrees relative to the initial position shown in FIG. 18A. Accordingly, paddle feature (1074) is rotated to a position such that protrusion (1034) of trigger (1032) is no longer impeded by paddle feature (1074). The user may then fire instrument (900).

Figure 19A:
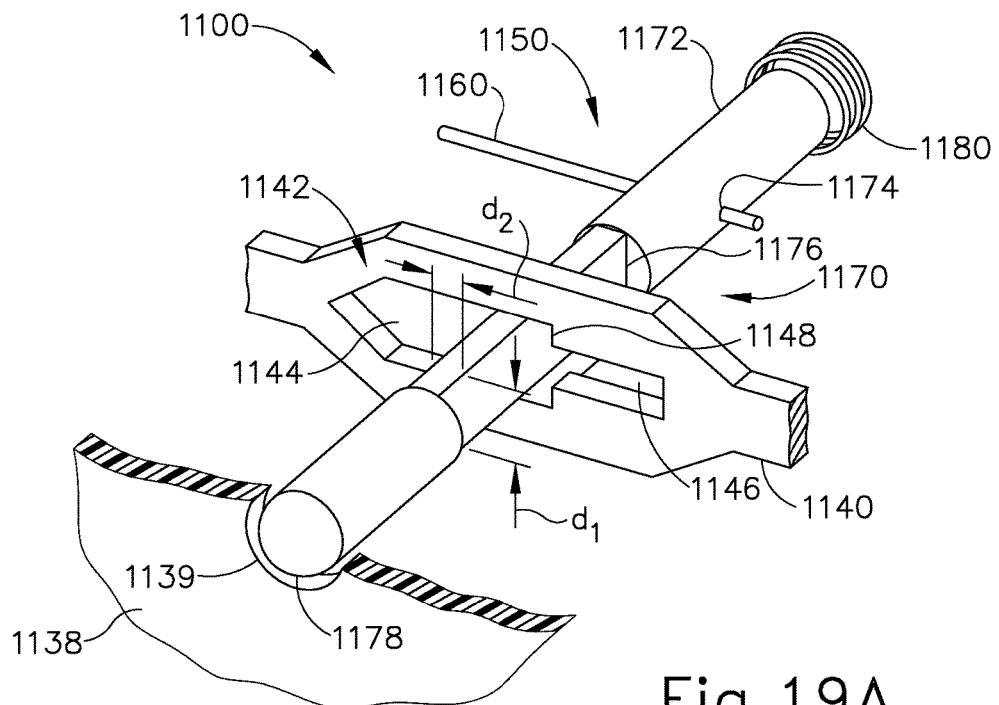
FIG. 19A depicts a partial perspective view of yet another exemplary lockout button assembly with a button shown in a first position and an anvil pin inserted therethrough.
Figure 19B:
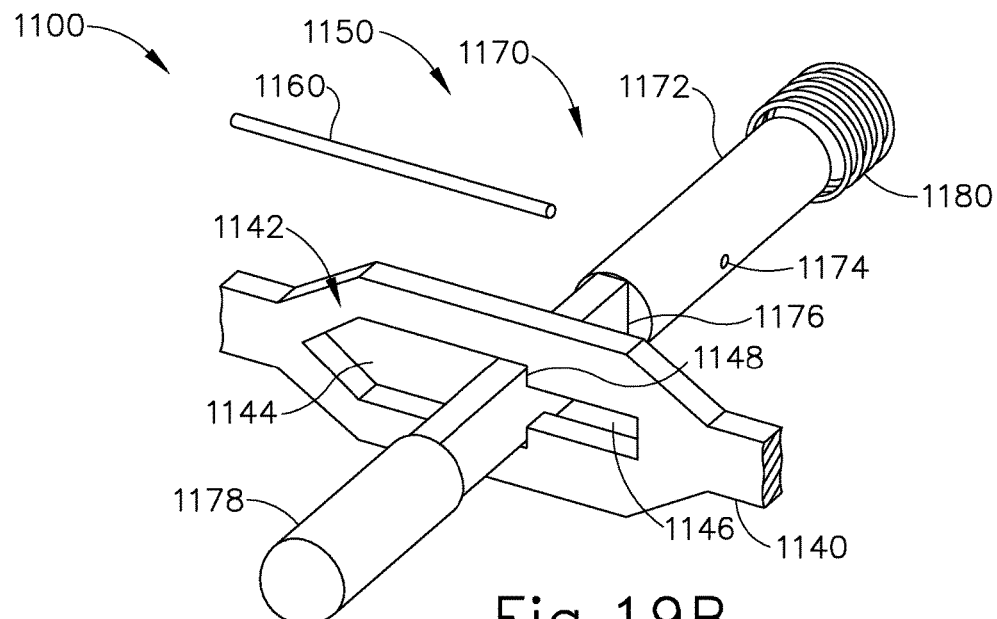
FIG. 19B depicts a partial perspective view of the lockout button assembly of FIG. 19A showing the anvil pin removed.
Figure 19C:
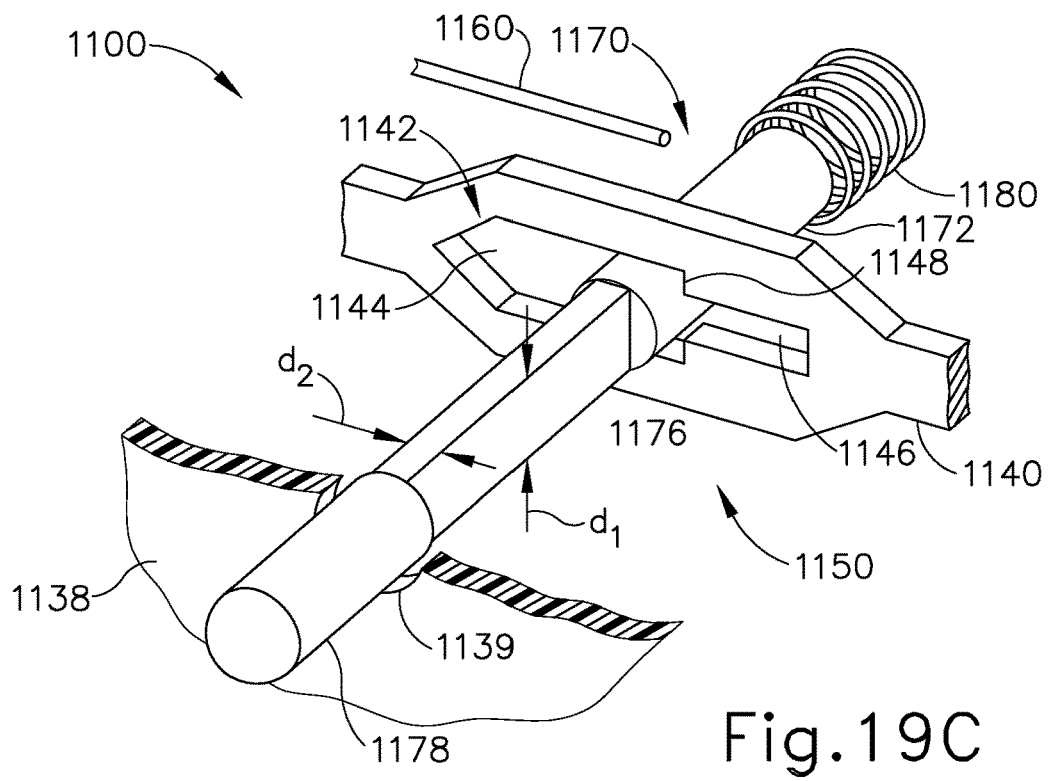
FIG. 19C depicts a partial perspective view of the lockout button assembly of FIG. 19A showing button actuated to a second position.

FIGS. 19A-19F depict yet another exemplary surgical instrument (1100) having an exemplary lockout button assembly (1150). Referring initially to FIG. 19A, lockout button assembly (1150) comprises an anvil sensing pin (1160) coupled to an anvil sensing rod (not shown) that extends longitudinally into an actuator handle assembly to engage a button (1170). In the present example, button (1170) comprises an inner portion (1172), an intermediate portion (1176) and an outer portion (1178). A spring (1180) is associated with inner portion (1172) and biases button (1170) laterally relative to a body (1138) (a cut away portion of which is shown in FIGS. 19A and 19C, but is omitted in FIGS. 19B and 19D-F for clarity). In the present example, outer portion (1178) of button (1170) is initially positioned within an opening (1139) in body (1138) and is substantially flush with the exterior of body (1138) in the first position. Inner portion (1172) of button (1170) includes a hole (1174) that is configured to receive anvil sensing pin (1160). Of course it should be understood that hole (1174) may be formed in intermediate portion (1176) and/or outer portion (1178) or, in some versions, omitted entirely. Intermediate portion (1176) of the present example comprises a rectangular member defined by a first dimension d1 and a second dimension d2 such that d2 is less than d1. Intermediate portion (1176) will be described in more detail below. Inner portion (1172) and outer portion (1178) are depicted as cylindrical members having diameters that are substantially equal to first dimension d1, though this is merely optional and inner portion (1172) and/or outer portion (1178) may have other shapes and/or configurations as will be apparent to one of ordinary skill in the art in view of the teachings herein.

Surgical instrument (1100) also includes a firing rod (1140) having a stepped aperture (1142) formed therethrough and configured to receive button (1170). Firing rod (1140) is coupled to a trigger (not shown) and is operable to actuate a staple driver (not shown) of instrument (1100). In the present example, stepped aperture (1142) comprises a first portion (1144) and a second portion (1146) with a step (1148). First portion (1144) is sized to be substantially equal to first dimension d1 such that intermediate portion (1176) of button (1170) can actuate laterally through first portion (1144). Second portion (1146) is located proximally of first portion (1144) and is reduced in size by step (1148). Second portion (1146) is sized to be substantially equal to second dimension d2 of intermediate portion (1176) such that firing rod (1140) can actuate longitudinally relative to intermediate portion (1176) when button (1170) is rotated to a third position, shown in FIGS. 19D-19F and described in greater detail below.

As shown in FIG. 19A, initially anvil sensing pin (1160) is inserted through hole (1174) of inner portion (1172). In some versions, anvil sensing pin (1160) may be only partially inserted into hole (1174) and/or hole (1174) does not extend through inner portion (1172) of button (1170). In this first position, anvil sensing pin (1160) prevents spring (1180) from biasing button (1170) laterally to protrude outer portion (1178) out of body (1138) through opening (1139). In addition, intermediate portion (1176) is initially positioned such that intermediate member (1176) is positioned within first portion (1144) of stepped aperture (1142) and is oriented with first dimension d1 perpendicular to the vertical plane along which the central axis of firing rod (1140) extends. As shown in FIG. 19A, intermediate portion (1176) interferes with distal actuation of firing rod (1140) due to step (1148) abutting intermediate portion (1176).

Once an anvil, such as anvil (40) described above, is fully seated, anvil sensing pin (1160) is retracted distally relative to button (1170) to disengage from hole (1174), as shown in FIG. 19B. Spring (1180) urges button (1170) laterally relative to body (1138) (shown in FIG. 19A), such that outer portion (1178) protrudes through opening (1139) to a second position shown in FIG. 19C. In addition, with button (1170) in the second position, inner portion (1172) is positioned within first portion (1144) of stepped aperture (1142) such that firing rod (1140) cannot be actuated longitudinally relative to button (1170). In some versions, spring (1180) may be omitted and button (1170) may be manually actuated to the second position.

Figure 19D:
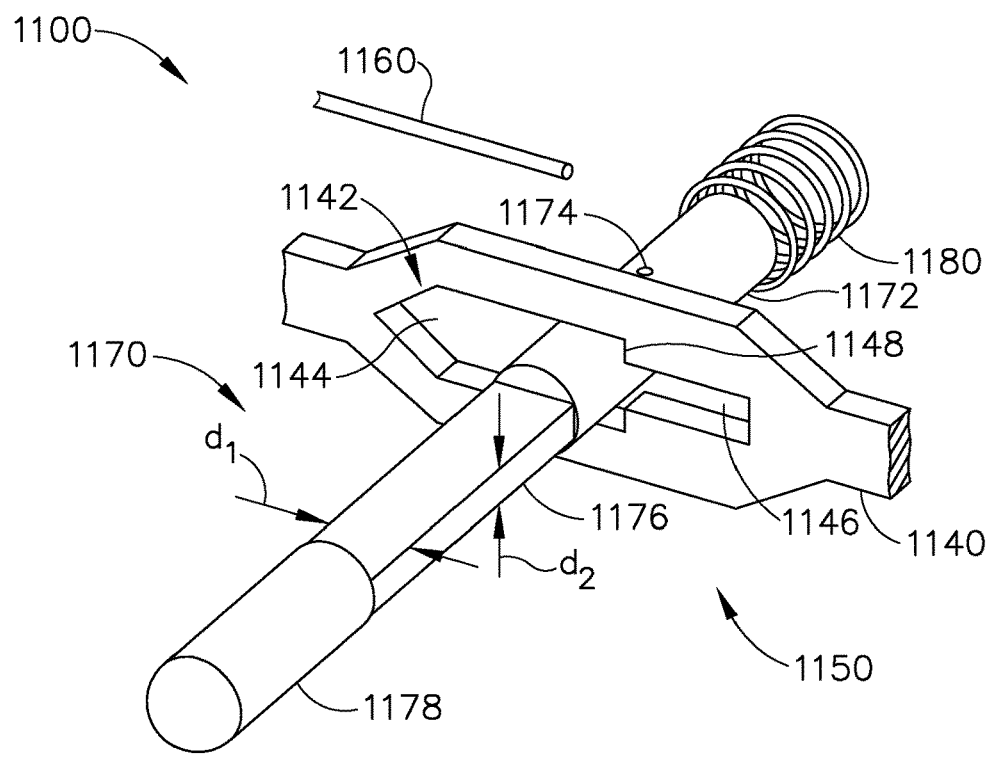
FIG. 19D depicts a partial perspective view of the lockout button assembly of FIG. 19A showing the button rotated to a third position.
Figure 19E:
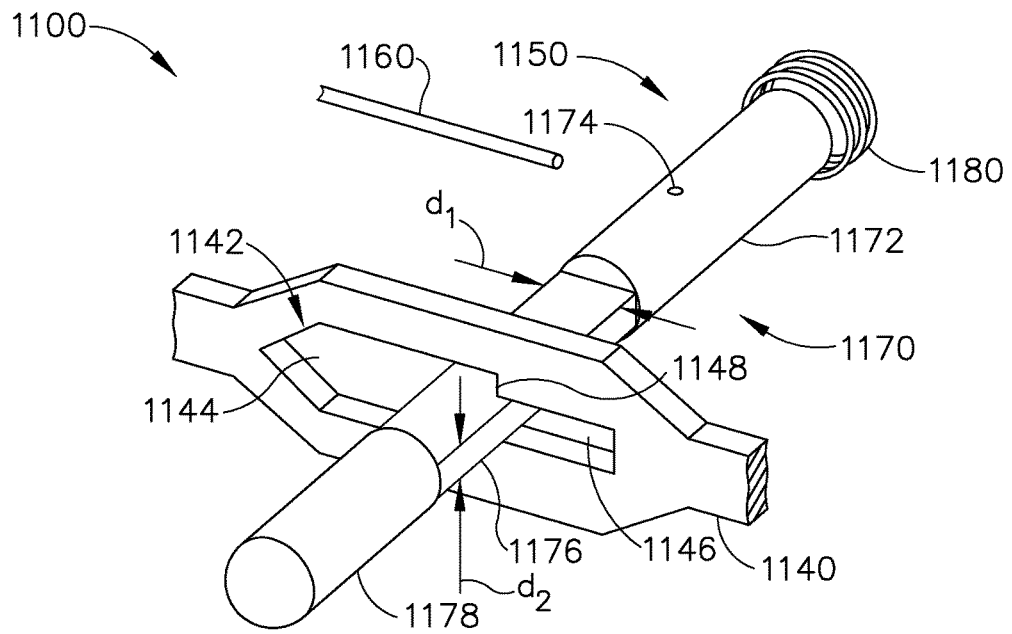
FIG. 19E depicts a partial perspective view of the lockout button assembly of FIG. 19A showing the button actuated to a fourth position.
Figure 19F:
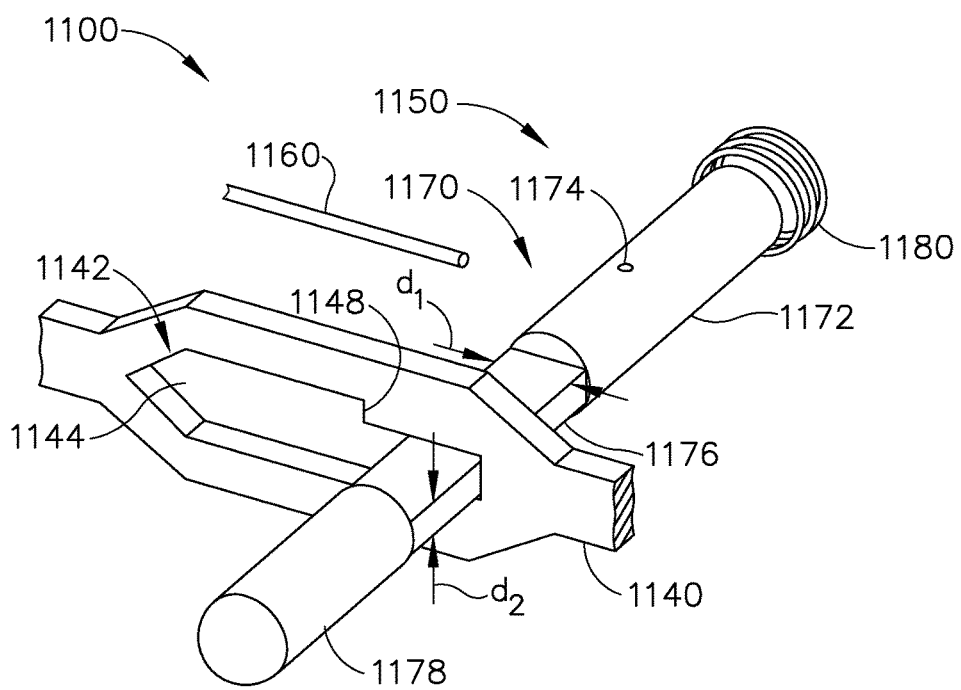
FIG. 19F depicts a partial perspective view of the lockout button assembly of FIG. 19A showing firing bar actuated relative to the button in the fourth position.

With outer portion (1178) protruding from body (1138) and thereby being exposed for grasping, the user rotates button (1170) to a third position, for instance by rotating button (1170) 90 degrees, such that intermediate portion (1176) is oriented with second dimension d2 perpendicular to the vertical plane along which the central axis of firing rod (1140) extends, as shown in FIG. 19D. In this position, inner portion (1172) is still positioned within first portion (1144) of stepped aperture (1142) such that firing rod (1140) cannot be actuated longitudinally relative to button (1170). The user then actuates button (1170) into body (1138) such that intermediate portion (1176) is aligned within stepped aperture (1142), as shown in FIG. 19E. As shown, with intermediate portion (1176) rotated to have second dimension d2 perpendicular to the vertical plane along which the central axis of firing rod (1140) extends, firing rod (1140) may then be actuated longitudinally relative to button (1170) since step (1148) and intermediate portion (1176) no longer abut and engage each other. Accordingly, the user may then fire instrument (1100). Of course other configurations and or assemblies will be apparent to one of ordinary skill in the art in view of the teachings herein.

ii. Exemplary Lockout Button Assembly Having a Palm Button

Figure 20A:
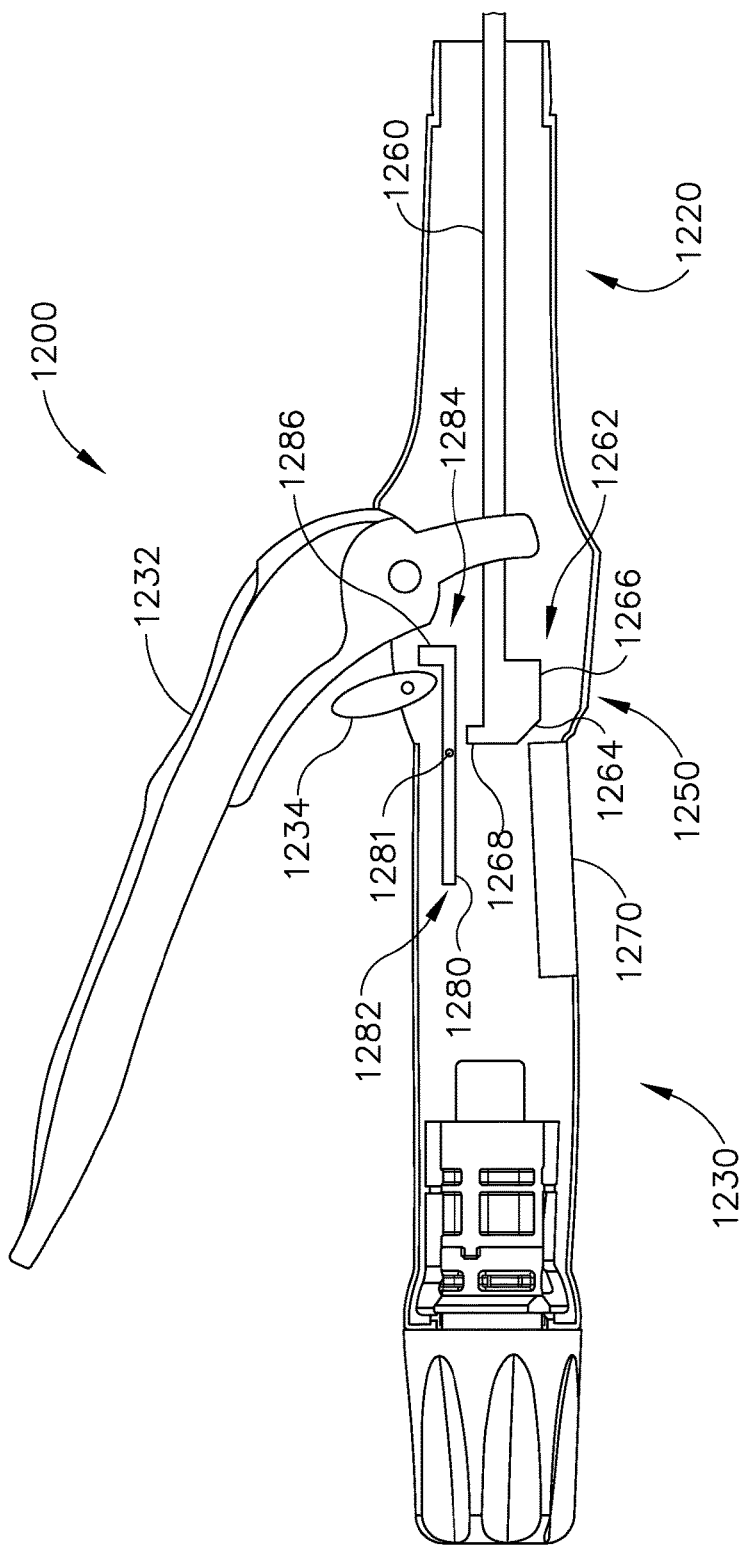
FIG. 20A depicts a side cross-sectional view of an exemplary surgical instrument having an alternative lockout button assembly shown in a first position.
Figure 20B:
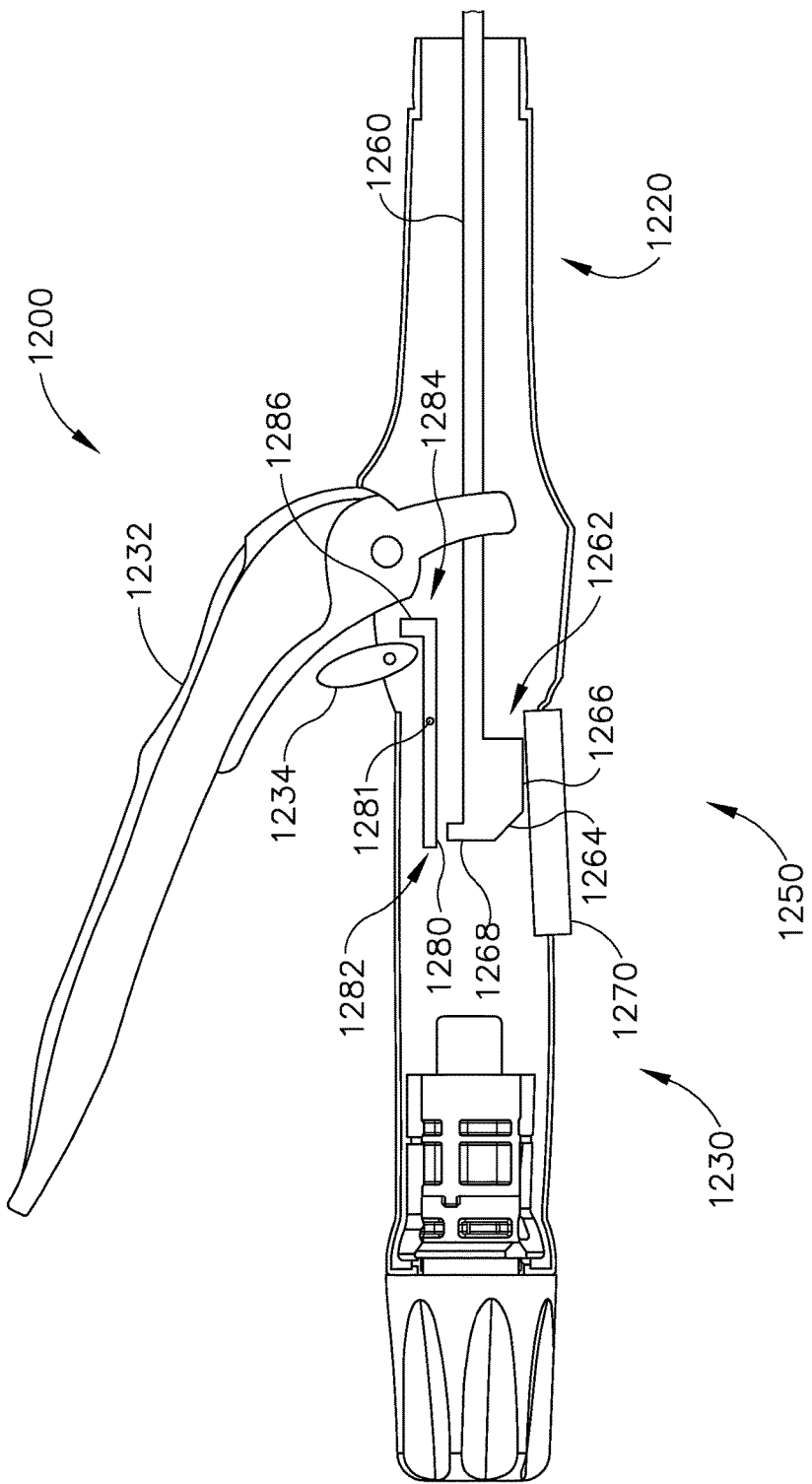
FIG. 20B depicts the alternative lockout button assembly of FIG. 20A shown in a second position.
Figure 20C:
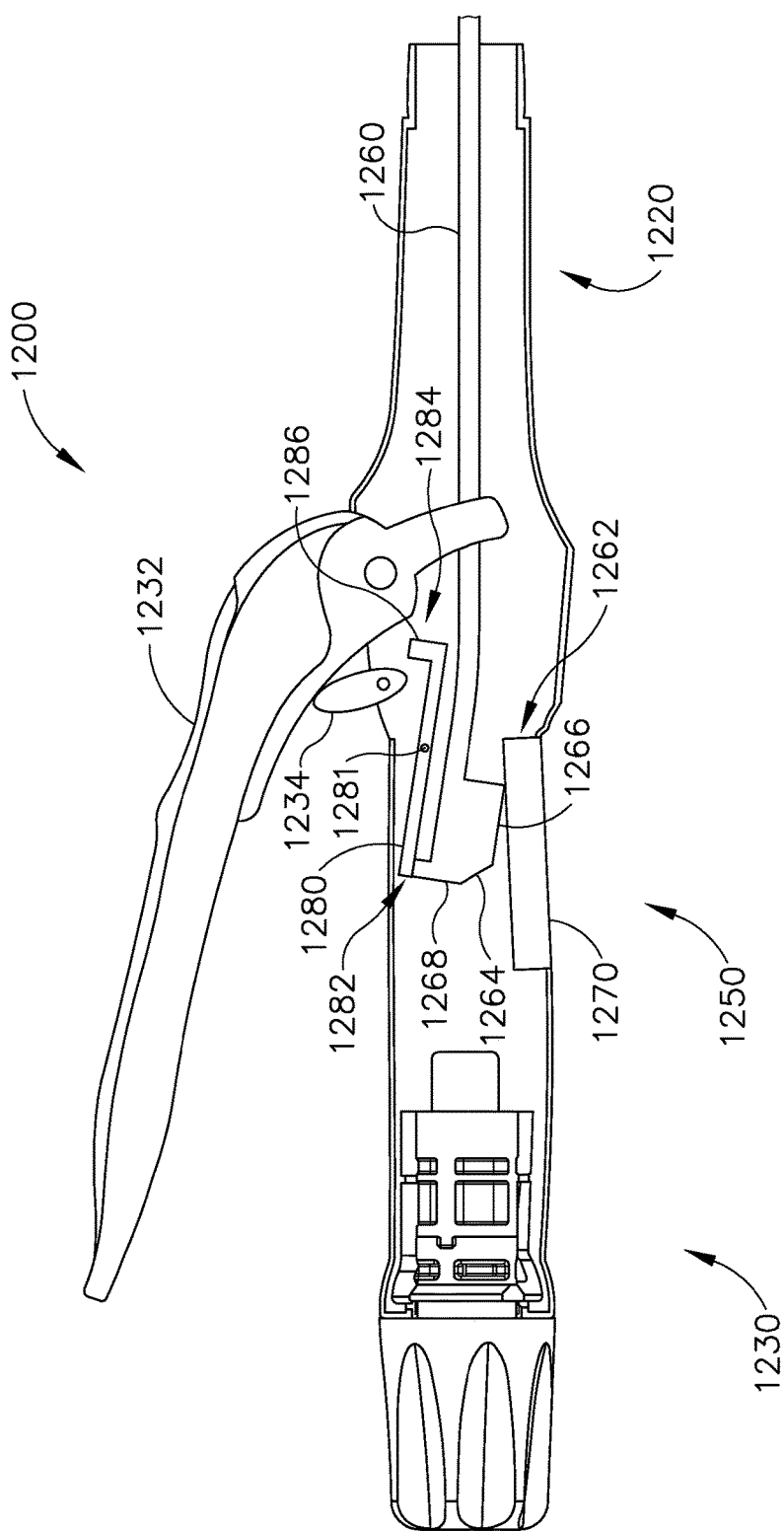
FIG. 20C depicts the alternative lockout button assembly of FIG. 20A showing a proximal end feature pivoting a pivot member.

FIG. 20A-20C depicts an exemplary alternative surgical instrument (1200) having exemplary lockout button assembly (1250). Referring initially to FIG. 20A, surgical instrument (1200) of the present example comprises a stapling head assembly (not shown), a shaft assembly (1220), and an actuator handle assembly (1230). Shaft assembly (1220) extends distally from actuator handle assembly (1230) and the stapling head assembly is coupled to a distal end of shaft assembly (1220). In brief, actuator handle assembly (1230) includes a trigger (1232) that is operable to actuate a staple driver (not shown) of the stapling head assembly to drive a plurality of staples (not shown) out of the stapling head assembly. The staples are bent to form completed staples by an anvil (not shown), such as anvil (40), that is attached to a trocar that extends out from the distal end of instrument (1200). Accordingly, tissue may be stapled utilizing instrument (1200). The stapling head assembly, shaft assembly (1220), and actuator handle assembly (1230) may be further constructed in accordance with stapling head assembly (20), shaft assembly (60), and actuator handle assembly (70) described above.

In the example shown, lockout button assembly (1250) of the present example comprises an anvil sensing shaft (1260), a palm button (1270), and a pivot member (1280). FIG. 20A depicts anvil sensing shaft (1260), palm button (1270), and pivot member (1280) in an initial, locked position. In this position, pivot member (1280) is configured to mechanically interfere with pivoting of a lockout feature (1234) such that trigger (1232) cannot be actuated. By way of example only, pivot member (1280) mechanically interferes with lockout feature (1234) via an arm (1286) that extends outwardly from a distal end (1284) of pivot member (1280). Lockout feature (1234) may be constructed in substantial accordance with lockout feature (82) described herein. Palm button (1270) in the present example is substantially flush with the exterior of instrument (1200), though this is merely optional and palm button (1270) may be inset or protrude relative to the exterior of instrument (1200). Anvil sensing shaft (1260) includes a proximal end feature (1262) configured to engage palm button (1270) and pivot member (1280). In the initial position shown in FIG. 20A, proximal end feature (1262) is disengaged from palm button (1270) and pivot member (1280). By way of example only, proximal end feature (1262) may be located distally of both palm button (1270) and pivot member (1280) such that a space is formed between palm button (1270) and pivot member (1280). Accordingly, even if a user attempts to actuate of palm button (1280) inwardly toward pivot member (1280) in this initial, locked position, palm button (1270) does not engage pivot member (1280). Thus, pivot member (1280) and arm (1286) remain in a position to mechanically interfere with lockout feature (1234). In some versions, pivot member (1280) may include a spring (not shown) to bias arm (1282) towards interfering with lockout feature (1234).

In the present example, proximal end feature (1262) includes a camming surface (1264), a button surface (1266), and a lever arm (1268). As shown in FIG. 20B, camming surface (1264) is operable to engage and cam palm button (1270) outwardly when anvil sensing shaft (1260) is actuated proximally relative to actuator handle assembly (1230), such as by attachment of an anvil and adjustment of the anvil and trocar into the "green zone." Palm button (1270) may thus provide a visual indicator that the anvil is properly attached and the device is within the operating range. Once palm button (1270) is cammed outwardly, at least part of palm button (1270) is adjacent to button surface (1266) such that palm button (1270) may engage button surface (1266) when palm button (1270) is pushed inwardly. In addition, lever arm (1268) of proximal end feature (1262) is aligned with a proximal end (1282) of pivot member (1280). Anvil sensing shaft (1260) may be further constructed in accordance with the teachings for anvil sensing tube (622) described herein, though it should be understood that any of the foregoing anvil detecting assemblies may be used in addition or in the alternative to anvil sensing shaft (1260).

When palm button (1270) and proximal end feature (1262) are aligned, as shown in FIG. 20B, the user presses palm button (1270) inwardly, thereby engaging lever arm (1268) with proximal end (1282) of pivot member (1280). Accordingly, when lever arm (1268) pivots pivot member (1280) about pivot (1281) by a predetermined amount, shown in FIG. 20C, arm (1286) no longer mechanically interferes with lockout feature (1234). The user may then pivot lockout feature (1234) to unlock trigger (1232) to fire instrument (1200). While one merely exemplary configuration for a lockout assembly (1250) having a palm button (1270) has been described, still further configurations will be apparent to one of ordinary skill in the art in view of the teachings herein. For instance, in some versions proximal end feature (1262) omits camming surface (1264) and palm button (1270) does not cam outwardly relative to the exterior of instrument (1200).

iii. Exemplary Lockout Button Assembly Having an Interlock Assembly

Figure 21A:
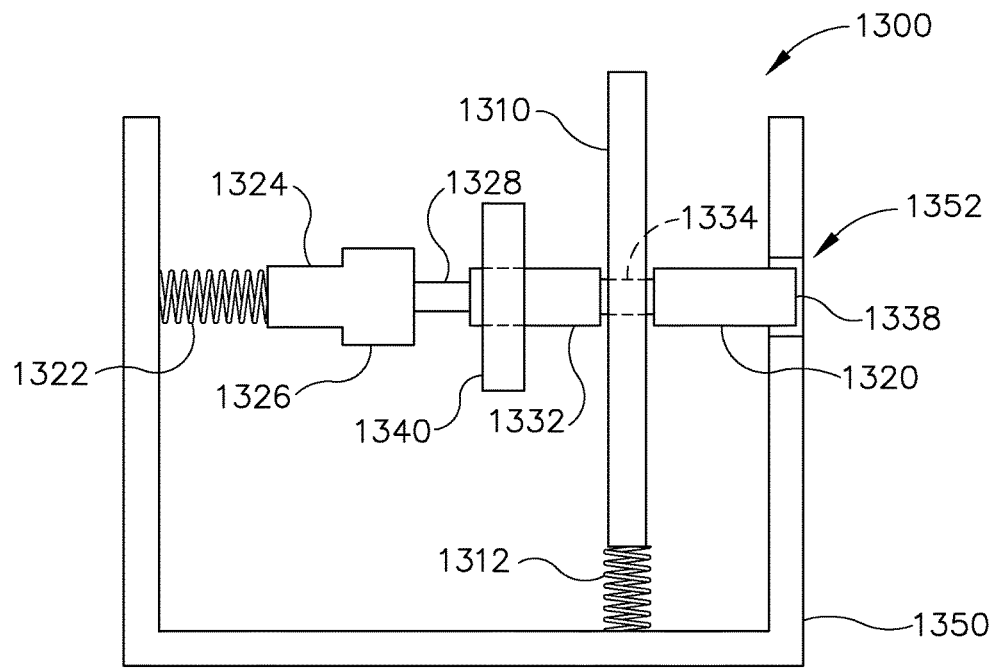
FIG. 21A depicts a schematic view of an exemplary interlock safety assembly shown in a locked position.

FIGS. 21A-23 depict yet another exemplary lockout button assembly (1300) comprising a spring-loaded push rod (1310), a spring-loaded pin (1320), and a pivotable lockout feature (1340). FIG. 21A, depicts spring-loaded push rod (1310), spring-loaded pin (1320), and pivotable lockout feature (1340) shown in an initial or locked position and contained within a body (1350) of an exemplary surgical instrument, such as instrument (10) described above. In the present example, body (1350) includes a pin hole (1352) sized to permit an outer portion (1338) of pin (1320) to extend therethrough. In some versions, pin hole (1352) may be sized to permit outer portion (1338) to extend therethrough, but comprises a smaller diameter than an intermediate portion (1332), thereby only permitting outer portion (1338) to protrude through. Of course it should be understood that pin hole (1352) is merely optional and may be omitted in some versions. Body (1350) may be further constructed in accordance with at least some of the teachings for body (72) described above.

Figure 22:
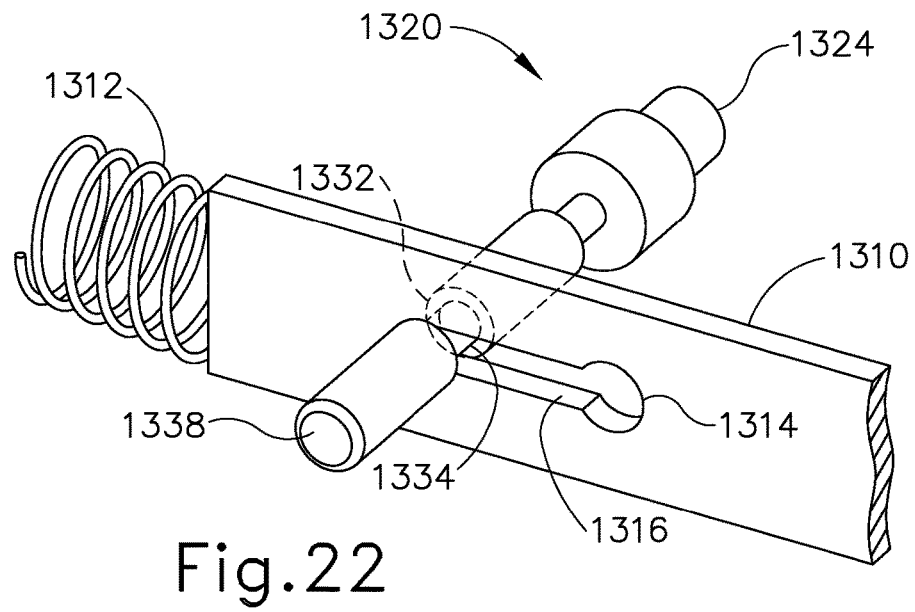
FIG. 22 depicts an enlarged partial perspective view of the interlock safety assembly of FIG. 21A showing an exemplary anvil rod in the locked position.
Figure 23:
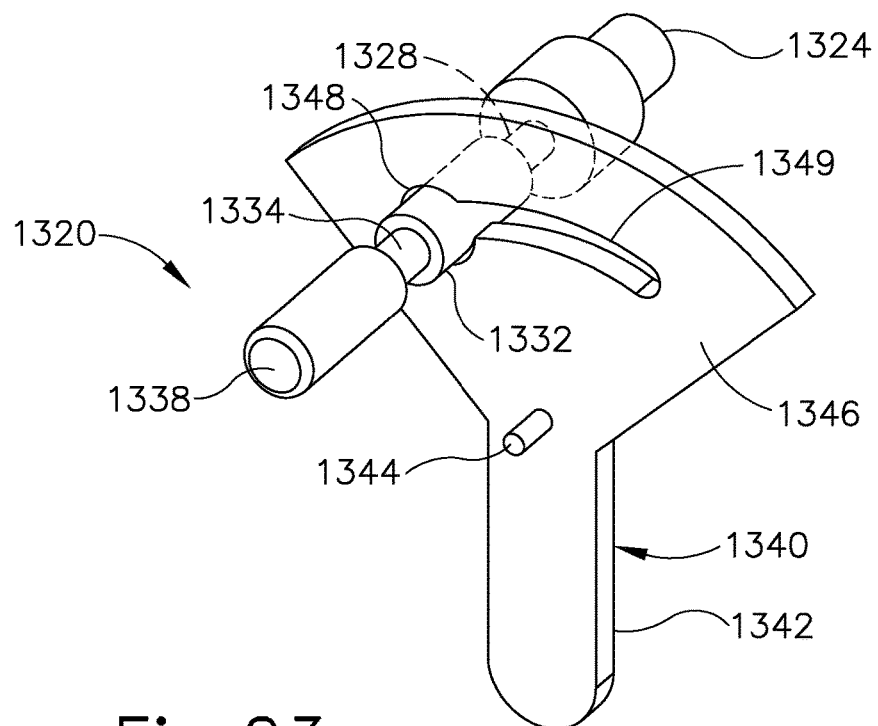
FIG. 23 depicts an enlarged partial perspective view of the interlock safety assembly of FIG. 21A showing an exemplary safety lever in the locked position.

Referring first to spring-loaded push rod (1310), push rod (1310) comprises an elongated rod extending longitudinally within a surgical instrument. A spring (1312) engages a proximal end of push rod (1310) to provide a distal bias. By way of example only, push rod (1310) may be configured to be actuated proximally when an anvil, such as anvil (40) is coupled to a trocar, such as trocar (38), and both the anvil and trocar are actuated into the operating range or "green zone" described above. Referring to FIG. 22 briefly, push rod (1310) includes a lateral hole (1314) and a longitudinal slot (1316) formed through push rod (1310). In the present example, lateral hole (1314) is sized to permit an intermediate portion (1332) of pin (1320) to pass through lateral hole (1314). Longitudinal slot (1316) is sized to permit an intermediate axle (1334) of pin (1320) to slide along longitudinal slot (1316). As shown in FIG. 22, pin (1320) and push rod (1310) are shown in the initial or locked position with push rod (1310) actuated distally via spring (1312), thereby laterally restraining pin (1320) with axle (1334) within slot (1316). In addition, or in the alternative, push rod (1310) may be constructed in accordance with the teachings for anvil sensing tube (622) described herein, though it should be understood that any of the foregoing anvil detecting assemblies may be incorporated into the present lockout button assembly (1300). Still other configurations for push rod (1310) will be apparent to one of ordinary skill in the art in view of the teachings herein.

FIG. 21A also depicts pin (1320) coupled to a spring (1322) such that pin (1320) is biased laterally toward pin hole (1352). Pin (1320) comprises an inner portion (1324), an inner axle (1328), an intermediate portion (1332), an intermediate axle (1334), and an outer portion (1338). In the present example, intermediate portion (1332) and outer portion (1338) are substantially dimensioned the same while inner portion (1324) includes an enlarged portion (1326). Of course it should be understood that this is merely optional. In some versions, inner portion (1324), intermediate portion (1332), and outer portion (1338) are all substantially dimensioned the same. In other versions, inner portion (1324), intermediate portion (1332), and outer portion (1338) all comprise different sizes and/or shapes. Accordingly, the lateral actuation of pin (1320) may be controlled by having varying sizes and/or shapes for inner portion (1324), intermediate portion (1332), and outer portion (1338). Inner axle (1328) couples inner portion (1324) to intermediate portion (1332) and is substantially smaller than either inner portion (1324) and/or intermediate portion (1332). In the present example, axle (1328) is configured to permit lockout feature (1340) to be pivoted while axle (1328) rides within an arcuate slot (1349), described in greater detail below. Intermediate axle (1334) couples intermediate portion (1332) to outer portion (1338) and is substantially smaller than either intermediate portion (1332) and/or outer portion (1338). In the present example, axle (1334) is configured to permit push rod (1310) to be actuated proximally relative to axle (1334) while axle (1334) rides within longitudinal slot (1316), described above.

Lockout feature (1340) of the present example comprises an arm (1342), a pivot member (1344), and a main body (1346). Arm (1342) is configured to abut a trigger (not shown) in a substantially similar manner to lockout feature (82) described above. Pivot member (1344) is configured to couple to a portion of body (1350), such as a recess, to permit lockout feature (1340) to be pivoted relative to body (1350). Main body (1346) comprises a sector, or pie-shaped, component having a hole (1348) and an arcuate slot (1349). Hole (1348) is sized to permit passage of intermediate portion (1332) of pin (1320) through hole (1348), but does not permit enlarged portion (1326) of inner portion (1324) to pass through. Arcuate slot (1349) is configured to permit inner axle (1328) to be slidably received within arcuate slot (1349). Accordingly, when inner axle (1328) is within hole (1348), such as that shown in FIG. 21B, lockout feature (1340) may be pivoted such that arcuate slot (1349) slides about inner axle (1328). Accordingly, when lockout feature (1340) is pivoted, arm (1342) no longer impedes actuation of the trigger, thereby allowing the user to fire the instrument. When lockout feature (1340) is in the first or locked position shown in FIGS. 21A and 23, lockout feature (1340) prevents the trigger from actuating and lockout feature (1340) is prevented from pivoting via the interference provided by the presence of intermediate portion (1332) of pin (1320) within hole (1348). Of course still further configurations for lockout feature (1340) will be apparent to one of ordinary skill in the art in view of the teachings herein.

Figure 21B:
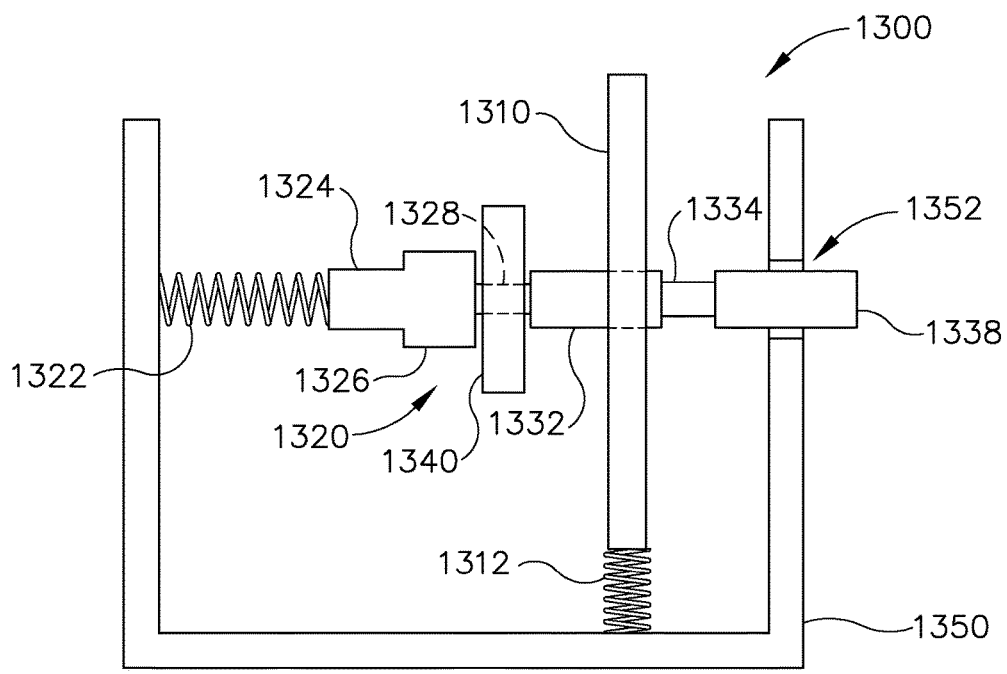
FIG. 21B depicts a schematic view of the interlock safety assembly of FIG. 21A shown in an unlocked position.

Referring now to the sequence depicted in FIGS. 21A-21B, initially spring-loaded push rod (1310), spring-loaded pin (1320), and pivotable lockout feature (1340) are in an initial or locked position. In this position, arm (1346) of lockout feature (1340) inhibits actuation of the trigger, lockout feature (1340) is prevented from pivoting because of the presence of intermediate portion (1332) within hole (1348), and pin (1320) is prevented from laterally actuating via spring (1322) because intermediate portion (1332) abuts push rod (1310) and is not aligned with lateral hole (1314). In the example shown, outer portion (1338) is within pin hole (1352) and is flush with the exterior of body (1350). When the user attaches an anvil, such as anvil (40), to a trocar, such as trocar (38), anvil may engage a distal end of push rod (1310) and begin to actuate push rod (1310) proximally against the bias provided by spring (1312). As noted with some of the foregoing examples, spring (1312)

may provide a sufficient distal force such that the anvil is ejected off of the trocar if the anvil is not fully seated. As the anvil is coupled to the trocar, longitudinal slot (1316) begins to slide proximally relative to intermediate axle (1334) to move lateral hole (1314) into closer alignment with intermediate portion (1332). Once the anvil and trocar are positioned within the operating range or "green zone," lateral hole (1314) and intermediate portion (1332) align. Spring (1322) urges pin laterally, thereby pushing intermediate portion (1332) into lateral hole (1314) and aligns inner axle (1328) with arcuate slot (1349) of lockout feature (1340), as shown in FIG. 21B. Enlarged portion (1326) abuts lockout feature (1340) to prevent spring (1322) from ejecting pin (1320) too far or out of the device. With inner axle (1328) and arcuate slot (1349) aligned, the user may pivot lockout feature (1340) about pivot member (1344), thereby releasing the trigger and permitting the user to fire the instrument. In some versions, a rotational spring (not shown) may be coupled to lockout feature (1340) to automatically pivot lockout feature (1340), though this is merely optional. In the present example, spring (1322) also extends outer portion (1338) of pin (1320) out of pin hole (1352). The protrusion of outer portion (1338) through pin hole (1352) can be used as a visual indicator by the user that the instrument is within the operating range such that lockout feature (1340) may be pivoted to release the trigger. Of course, in some versions outer portion (1338) and/or pin hole (1352) may be omitted. Still further configurations for lockout button assembly (1300) will be apparent to one of ordinary skill in the art in view of the teachings herein.

It should be understood that any one or more of the teachings, expressions, embodiments, examples, etc. described herein may be combined with any one or more of the other teachings, expressions, embodiments, examples, etc. that are described herein. The above-described teachings, expressions, embodiments, examples, etc. should therefore not be viewed in isolation relative to each other. Various suitable ways in which the teachings herein may be combined will be readily apparent to those of ordinary skill in the art in view of the teachings herein. Such modifications and variations are intended to be included within the scope of the claims.

It should be appreciated that any patent, publication, or other disclosure material, in whole or in part, that is said to be incorporated by reference herein is incorporated herein only to the extent that the incorporated material does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

Embodiments of the present invention have application in conventional endoscopic and open surgical instrumentation as well as application in robotic-assisted surgery. For instance, those of ordinary skill in the art will recognize that various teaching herein may be readily combined with various teachings of U.S. Pat. No. 6,783,524, entitled "Robotic Surgical Tool with Ultrasound Cauterizing and Cutting Instrument," published Aug. 31, 2004, the disclosure of which is incorporated by reference herein.

By way of example only, embodiments described herein may be processed before surgery. First, a new or used instrument may be obtained and if necessary cleaned. The instrument may then be sterilized. In one sterilization technique, the instrument is placed in a closed and sealed container, such as a plastic or TYVEK bag. The container and instrument may then be placed in a field of radiation that can penetrate the container, such as gamma radiation, x-rays, or high-energy electrons. The radiation may kill bacteria on the instrument and in the container. The sterilized instrument may then be stored in the sterile container. The sealed container may keep the instrument sterile until it is opened in a medical facility. A device may also be sterilized using any other technique known in the art, including but not limited to beta or gamma radiation, ethylene oxide, or steam.

Embodiments of the devices disclosed herein can be reconditioned for reuse after at least one use. Reconditioning may include any combination of the steps of disassembly of the device, followed by cleaning or replacement of particular pieces, and subsequent reassembly. In particular, embodiments of the devices disclosed herein may be disassembled, and any number of the particular pieces or parts of the devices may be selectively replaced or removed in any combination. Upon cleaning and/or replacement of particular parts, embodiments of the devices may be reassembled for subsequent use either at a reconditioning facility, or by a surgical team immediately prior to a surgical procedure. Those skilled in the art will appreciate that reconditioning of a device may utilize a variety of techniques for disassembly, cleaning/replacement, and reassembly. Use of such techniques, and the resulting reconditioned device, are all within the scope of the present application.

Having shown and described various embodiments of the present invention, further adaptations of the methods and systems described herein may be accomplished by appropriate modifications by one of ordinary skill in the art without departing from the scope of the present invention. Several of such potential modifications have been mentioned, and others will be apparent to those skilled in the art. For instance, the examples, embodiments, geometries, materials, dimensions, ratios, steps, and the like discussed above are illustrative and are not required. Accordingly, the scope of the present invention should be considered in terms of the following claims and is understood not to be limited to the details of structure and operation shown and described in the specification and drawings.

We claim:

1. An apparatus for stapling tissue, the apparatus comprising:
 (a) a body; and
 (b) a stapling head assembly comprising:
  (i) a staple driver configured to drive staples in response to an input from the body,
  (ii) a rod extending along an axis, and
  (iii) an anvil detection feature coupled to the rod, wherein the anvil detection feature is configured to move from a first position to a second position relative to the axis, wherein the anvil detection feature is configured to engage the staple driver and thereby prevent the staple driver from driving staples when the anvil detection feature is in the first position, wherein the anvil detection feature is configured to disengage the staple driver and thereby permit the staple driver to drive staples when the anvil detection feature is in the second position.

2. The apparatus of claim 1, wherein the anvil detection feature comprises a moveable member that is resiliently biased toward the first position.

3. The apparatus of claim 2, wherein the moveable member comprises a hinged tab operable to pivot relative to the rod between the first position and the second position.

4. The apparatus of claim 2, further comprising a spring coupled to the moveable member, wherein the spring is configured to resiliently bias the moveable member toward the first position.

5. The apparatus of claim 2, wherein the moveable member comprises a pair of spring clips, wherein the spring clips are operable to pivot relative to the rod between the first position and the second position.

6. The apparatus of claim 5, wherein the spring clips are disposed within a slot formed in the rod.

7. The apparatus of claim 5, wherein the staple driver includes a pair of notches, wherein the spring clips are configured to engage the notches when in the first position to thereby prevent the staple driver from advancing distally to fire staples.

8. The apparatus of claim 1, wherein the anvil detection feature is configured to be positioned outwardly relative to the axis when the anvil detection feature is in the first position, wherein the anvil detection feature is configured to be positioned inwardly relative to the axis when the anvil detection feature is in the second position.

9. The apparatus of claim 1, further comprising an anvil, wherein the anvil is configured to couple with the rod, wherein the anvil detection feature is configured to move to the second position in response to the anvil being coupled with the rod.

10. The apparatus of claim 9, wherein the anvil comprises a hollow shaft, wherein the hollow shaft is configured to slide over the rod to couple the anvil and the rod.

11. The apparatus of claim 10, wherein the hollow shaft is configured to engage the anvil detection feature only when the hollow shaft is fully seated on the rod.

12. The apparatus of claim 10, wherein the anvil detection feature is configured to be urged to the second position in response to the hollow shaft being slid over the rod.

13. The apparatus of claim 1, wherein the anvil detection feature is in communication with a lockout feature of the body.

14. The apparatus of claim 13, further comprising a trigger pivotably mounted to the body, wherein the trigger is operable to actuate the staple driver distally relative to the body, wherein the lockout feature is configured to prevent pivoting of the trigger when the anvil detection feature is in the first position.

15. The apparatus of claim 1, wherein the anvil detection feature is positioned on an exterior surface of the rod.

16. An apparatus for stapling tissue, the apparatus comprising:
  (a) a body;
  (b) an anvil;
  (c) an actuator operable to move the anvil relative to the body; and
  (d) a stapling head assembly comprising:
    (i) a rod extending along an axis, wherein a proximal end of the rod is coupled with the actuator and a distal end of the rod is configured to couple with the anvil, wherein the rod is configured to translate along the axis between a distal position and a proximal position to thereby move the anvil between a distal position and a proximal position in response to an input from the actuator,
    (ii) a staple driver configured to drive staples toward the anvil in response to an input from the body, wherein the anvil is configured to deform the driven staples when the anvil is in the proximal position, and
    (iii) an anvil detection feature coupled to the rod, wherein the anvil detection feature is movable from a first position to a second position, wherein the rod is prevented from translating to the proximal position when the anvil detection feature is in the first position, wherein the rod is permitted to translate to the proximal position when the anvil detection feature is in the second position,
  wherein the rod and the anvil detection feature are fixed axially relative to the actuator.

17. The apparatus of claim 16, wherein the anvil is configured to engage the anvil detection feature and thereby drive the anvil detection feature from the first position to the second position in response to the anvil being fully coupled with the rod.

18. The apparatus of claim 16, wherein the anvil detection feature is configured to pivot from the first position to the second position.

19. The apparatus of claim 16, wherein the anvil detection feature comprises a resilient tab.

20. An apparatus for stapling tissue, the apparatus comprising:
  (a) an actuator handle assembly comprising:
    (i) a body, and
    (ii) a trigger pivotably mounted to the body;
  (b) an anvil; and
  (c) a stapling head assembly comprising:
    (i) a staple driver,
    (ii) a rod, and
    (iii) an anvil detection feature slidably disposed over the rod, wherein the anvil detection feature is movable relative to the rod from a first position to a second position in response to engagement of the anvil with the rod;
  wherein the trigger is operable to actuate the staple driver distally relative to the actuator handle assembly when the anvil detection feature is in the second position;
  wherein the trigger is prevented from actuating the staple driver distally relative to the actuator handle assembly when the anvil detection feature is in the first position.

* * * * *